US011752342B2

(12) United States Patent
Bakker et al.

(10) Patent No.: US 11,752,342 B2
(45) Date of Patent: Sep. 12, 2023

(54) SYSTEM FOR NEUROMODULATION

(71) Applicant: ONWARD MEDICAL N.V., Eindhoven (NL)

(72) Inventors: Jurriaan Bakker, Eindhoven (NL); Hans Pflug, Eindhoven (NL); Robin Brouns, Eindhoven (NL); Vincent Delattre, Eindhoven (NL)

(73) Assignee: Onward Medical N.V., Eindhoven (NL)

( * ) Notice: Subject to any disclaimer, the term of this patent is extended or adjusted under 35 U.S.C. 154(b) by 188 days.

(21) Appl. No.: 16/788,175

(22) Filed: Feb. 11, 2020

(65) Prior Publication Data

US 2020/0254260 A1 Aug. 13, 2020

(30) Foreign Application Priority Data

Feb. 12, 2019 (EP) ..................................... 19156617

(51) Int. Cl.
*A61N 1/36* (2006.01)
*A61N 1/372* (2006.01)

(52) U.S. Cl.
CPC ..... *A61N 1/36139* (2013.01); *A61N 1/37282* (2013.01)

(58) Field of Classification Search
CPC .......................... A61N 1/36139; A61N 1/37282
USPC ........................................................ 607/117
See application file for complete search history.

(56) References Cited

U.S. PATENT DOCUMENTS

| 2,868,343 A | 1/1959 | Sproul |
| 3,543,761 A | 12/1970 | Bradley |
| 3,650,277 A | 3/1972 | Sjostrand et al. |
| 3,662,758 A | 5/1972 | Glover |
| 3,724,467 A | 4/1973 | Avery et al. |
| 4,044,774 A | 8/1977 | Corbin et al. |
| 4,102,344 A | 7/1978 | Conway et al. |
| 4,141,365 A | 2/1979 | Fischell et al. |
| 4,285,347 A | 8/1981 | Hess |
| 4,340,063 A | 7/1982 | Maurer |
| 4,379,462 A | 4/1983 | Borkan et al. |
| 4,398,537 A | 8/1983 | Holmbo |

(Continued)

FOREIGN PATENT DOCUMENTS

| AU | 2012204526 | 9/2016 |
| CA | 2856202 A1 | 5/2013 |

(Continued)

OTHER PUBLICATIONS

Bizzi, E. et al., "Modular Organization of Motor Behavior," Trends in Neurosciences, vol. 18, No. 10, Oct. 1995, 8 pages.

(Continued)

*Primary Examiner* — Erin M Piateski
(74) *Attorney, Agent, or Firm* — Finnegan, Henderson, Farabow, Garrett & Dunner, LLP

(57) ABSTRACT

Systems and methods for a neuromodulation system are provided. In one example, the neuromodulation system includes a stimulation element, a stimulation controller, and a stimulation feedback acquisition system that includes a reference trigger input module configured such that the temporal relationship between a provided stimulation via the stimulation element and the stimulation controller, and a stimulation response received by the stimulation feedback acquisition system can be characterized.

18 Claims, 7 Drawing Sheets

(56) References Cited

U.S. PATENT DOCUMENTS

| | | |
|---|---|---|
| 4,414,986 A | 11/1983 | Dickhudt et al. |
| 4,538,624 A | 9/1985 | Tarjan |
| 4,549,556 A | 10/1985 | Tarjan et al. |
| 4,559,948 A | 12/1985 | Liss et al. |
| 4,569,352 A | 2/1986 | Petrofsky et al. |
| 4,573,481 A | 3/1986 | Bullara |
| 4,724,842 A | 2/1988 | Charters |
| 4,800,898 A | 1/1989 | Hess et al. |
| 4,934,368 A | 6/1990 | Lynch |
| 4,969,452 A | 11/1990 | Petrofsky et al. |
| 5,002,053 A | 3/1991 | Garcia-Rill et al. |
| 5,018,631 A | 5/1991 | Reimer |
| 5,031,618 A | 7/1991 | Mullet |
| 5,066,272 A | 11/1991 | Eaton et al. |
| 5,081,989 A | 1/1992 | Graupe et al. |
| 5,121,754 A | 6/1992 | Mullett |
| 5,344,439 A | 9/1994 | Otten |
| 5,354,320 A | 10/1994 | Schaldach et al. |
| 5,366,813 A | 11/1994 | Berlin |
| 5,374,285 A | 12/1994 | Vaiani et al. |
| 5,417,719 A | 5/1995 | Hull et al. |
| 5,476,441 A | 12/1995 | Durfee et al. |
| 5,562,718 A | 10/1996 | Palermo |
| 5,643,330 A | 7/1997 | Holsheimer et al. |
| 5,733,322 A | 3/1998 | Starkebaum |
| 5,983,141 A | 11/1999 | Sluijter et al. |
| 6,058,331 A | 5/2000 | King |
| 6,066,163 A | 5/2000 | John |
| 6,104,957 A | 8/2000 | Alo et al. |
| 6,122,548 A | 9/2000 | Starkebaum et al. |
| 6,308,103 B1 | 10/2001 | Gielen |
| 6,319,241 B1 | 11/2001 | King et al. |
| 6,463,327 B1 | 10/2002 | Lurie et al. |
| 6,470,213 B1 | 10/2002 | Alley |
| 6,500,110 B1 | 12/2002 | Davey et al. |
| 6,503,231 B1 | 1/2003 | Prausnitz et al. |
| 6,505,074 B2 | 1/2003 | Boveja et al. |
| 6,516,227 B1 | 2/2003 | Meadows et al. |
| 6,551,849 B1 | 4/2003 | Kenney |
| 6,587,724 B2 | 7/2003 | Mann |
| 6,662,053 B2 | 12/2003 | Borkan |
| 6,666,831 B1 | 12/2003 | Edgerton et al. |
| 6,685,729 B2 | 2/2004 | Gonzalez |
| 6,748,276 B1 | 6/2004 | Daignault, Jr. et al. |
| 6,819,956 B2 | 11/2004 | DiLorenzo |
| 6,839,594 B2 | 1/2005 | Cohen et al. |
| 6,862,479 B1 | 3/2005 | Whitehurst et al. |
| 6,871,099 B1 | 3/2005 | Whitehurst et al. |
| 6,878,112 B2 | 4/2005 | Linberg et al. |
| 6,892,098 B2 | 5/2005 | Ayal et al. |
| 6,895,280 B2 | 5/2005 | Meadows et al. |
| 6,895,283 B2 | 5/2005 | Erickson et al. |
| 6,937,891 B2 | 8/2005 | Leinders et al. |
| 6,950,706 B2 | 9/2005 | Rodriguez et al. |
| 6,975,907 B2 | 12/2005 | Zanakis et al. |
| 6,988,006 B2 | 1/2006 | King et al. |
| 6,999,820 B2 | 2/2006 | Jordan |
| 7,020,521 B1 | 3/2006 | Brewer et al. |
| 7,024,247 B2 | 4/2006 | Gliner et al. |
| 7,035,690 B2 | 4/2006 | Goetz |
| 7,047,084 B2 | 5/2006 | Erickson et al. |
| 7,065,408 B2 | 6/2006 | Herman et al. |
| 7,096,070 B1 | 8/2006 | Jenkins et al. |
| 7,110,820 B2 | 9/2006 | Tcheng et al. |
| 7,125,388 B1 | 10/2006 | Reinkensmeyer et al. |
| 7,127,287 B2 | 10/2006 | Duncan et al. |
| 7,127,296 B2 | 10/2006 | Bradley |
| 7,127,297 B2 | 10/2006 | Law et al. |
| 7,149,773 B2 | 12/2006 | Haller et al. |
| 7,153,242 B2 | 12/2006 | Goffer |
| 7,184,837 B2 | 2/2007 | Goetz |
| 7,200,443 B2 | 4/2007 | Faul |
| 7,209,787 B2 | 4/2007 | DiLorenzo |
| 7,228,179 B2 | 6/2007 | Campen et al. |
| 7,239,920 B1 | 7/2007 | Thacker et al. |
| 7,251,529 B2 | 7/2007 | Greenwood-Van Meerveld |
| 7,252,090 B2 | 8/2007 | Goetz |
| 7,313,440 B2 | 12/2007 | Miesel |
| 7,324,853 B2 | 1/2008 | Ayal et al. |
| 7,330,760 B2 | 2/2008 | Heruth et al. |
| 7,337,005 B2 | 2/2008 | Kim et al. |
| 7,337,006 B2 | 2/2008 | Kim et al. |
| 7,381,192 B2 | 6/2008 | Brodard et al. |
| 7,415,309 B2 | 8/2008 | McIntyre |
| 7,463,927 B1 | 12/2008 | Chaouat |
| 7,463,928 B2 | 12/2008 | Lee et al. |
| 7,467,016 B2 | 12/2008 | Colborn |
| 7,493,170 B1 | 2/2009 | Segel et al. |
| 7,496,404 B2 | 2/2009 | Meadows et al. |
| 7,502,652 B2 | 3/2009 | Gaunt et al. |
| 7,536,226 B2 | 5/2009 | Williams et al. |
| 7,544,185 B2 | 6/2009 | Bengtsson |
| 7,584,000 B2 | 9/2009 | Erickson |
| 7,590,454 B2 | 9/2009 | Garabedian et al. |
| 7,603,178 B2 | 10/2009 | North et al. |
| 7,620,502 B2 | 11/2009 | Selifonov et al. |
| 7,628,750 B2 | 12/2009 | Cohen et al. |
| 7,647,115 B2 | 1/2010 | Levin et al. |
| 7,660,636 B2 | 2/2010 | Castel et al. |
| 7,697,995 B2 | 4/2010 | Cross, Jr. et al. |
| 7,725,193 B1 | 5/2010 | Chu |
| 7,729,781 B2 | 6/2010 | Swoyer et al. |
| 7,734,340 B2 | 6/2010 | de Ridder |
| 7,734,351 B2 | 6/2010 | Testerman et al. |
| 7,769,463 B2 | 8/2010 | Katsnelson |
| 7,797,057 B2 | 9/2010 | Harris |
| 7,801,601 B2 | 9/2010 | Maschino et al. |
| 7,813,803 B2 | 10/2010 | Heruth et al. |
| 7,813,809 B2 | 10/2010 | Strother et al. |
| 7,856,264 B2 | 12/2010 | Firlik et al. |
| 7,877,146 B2 | 1/2011 | Rezai et al. |
| 7,890,182 B2 | 2/2011 | Parramon et al. |
| 7,949,395 B2 | 5/2011 | Kuzma |
| 7,949,403 B2 | 5/2011 | Palermo et al. |
| 7,987,000 B2 | 7/2011 | Moffitt et al. |
| 7,991,465 B2 | 8/2011 | Bartic et al. |
| 8,019,427 B2 | 9/2011 | Moffitt |
| 8,050,773 B2 | 11/2011 | Zhu |
| 8,108,051 B2 | 1/2012 | Cross, Jr. et al. |
| 8,108,052 B2 | 1/2012 | Boling |
| 8,131,358 B2 | 3/2012 | Moffitt et al. |
| 8,135,473 B2 | 3/2012 | Miesel et al. |
| 8,155,750 B2 | 4/2012 | Jaax et al. |
| 8,168,481 B2 | 5/2012 | Hanaoka et al. |
| 8,170,660 B2 | 5/2012 | Dacey, Jr. et al. |
| 8,190,262 B2 | 5/2012 | Gerber et al. |
| 8,195,304 B2 | 6/2012 | Strother et al. |
| 8,214,048 B1 | 7/2012 | Whitehurst et al. |
| 8,229,565 B2 | 7/2012 | Kim et al. |
| 8,239,038 B2 | 8/2012 | Wolf, II |
| 8,260,436 B2 | 9/2012 | Gerber et al. |
| 8,271,099 B1 | 9/2012 | Swanson |
| 8,295,936 B2 | 10/2012 | Wahlstrand et al. |
| 8,311,644 B2 | 11/2012 | Moffitt et al. |
| 8,332,029 B2 | 12/2012 | Glukhovsky et al. |
| 8,332,047 B2 | 12/2012 | Libbus et al. |
| 8,346,366 B2 | 1/2013 | Arle et al. |
| 8,352,036 B2 | 1/2013 | DiMarco et al. |
| 8,355,791 B2 | 1/2013 | Moffitt |
| 8,355,797 B2 | 1/2013 | Caparso et al. |
| 8,364,273 B2 | 1/2013 | de Ridder |
| 8,369,961 B2 | 2/2013 | Christman et al. |
| 8,374,696 B2 | 2/2013 | Sanchez et al. |
| 8,412,345 B2 | 4/2013 | Moffitt |
| 8,428,728 B2 | 4/2013 | Sachs |
| 8,442,655 B2 | 5/2013 | Moffitt et al. |
| 8,452,406 B2 | 5/2013 | Arcot-Krishnamurthy et al. |
| 8,543,200 B2 | 9/2013 | Lane et al. |
| 8,588,884 B2 | 11/2013 | Hegde et al. |
| 8,626,300 B2 | 1/2014 | Demarais et al. |
| 8,700,145 B2 | 4/2014 | Kilgard et al. |
| 8,712,546 B2 | 4/2014 | Kim et al. |
| 8,740,825 B2 | 6/2014 | Ehrenreich et al. |
| 8,750,957 B2 | 6/2014 | Tang et al. |

(56) References Cited

U.S. PATENT DOCUMENTS

| | | |
|---|---|---|
| 8,768,481 B2 | 7/2014 | Lane |
| 8,805,542 B2 | 8/2014 | Tai et al. |
| 9,072,891 B1 | 7/2015 | Rao |
| 9,079,039 B2 | 7/2015 | Carlson et al. |
| 9,101,769 B2 | 8/2015 | Edgerton et al. |
| 9,205,259 B2 | 12/2015 | Kim et al. |
| 9,205,260 B2 | 12/2015 | Kim et al. |
| 9,205,261 B2 | 12/2015 | Kim et al. |
| 9,248,291 B2 | 2/2016 | Mashiach |
| 9,272,139 B2 | 3/2016 | Hamilton et al. |
| 9,272,143 B2 | 3/2016 | Libbus et al. |
| 9,283,391 B2 | 3/2016 | Ahmed |
| 9,314,630 B2 | 4/2016 | Levin et al. |
| 9,393,409 B2 | 7/2016 | Edgerton et al. |
| 9,409,023 B2 | 8/2016 | Burdick et al. |
| 9,415,218 B2 | 8/2016 | Edgerton et al. |
| 9,421,365 B2 | 8/2016 | Sumners et al. |
| 9,597,517 B2 | 3/2017 | Moffitt |
| 9,610,442 B2 | 4/2017 | Yoo et al. |
| 9,993,642 B2 | 6/2018 | Gerasimenko et al. |
| 10,092,750 B2 | 10/2018 | Edgerton et al. |
| 10,124,166 B2 | 11/2018 | Edgerton et al. |
| 10,137,299 B2 | 11/2018 | Lu et al. |
| 10,449,371 B2 | 10/2019 | Serrano Carmona |
| 10,751,533 B2 | 8/2020 | Edgerton et al. |
| 10,773,074 B2 | 9/2020 | Liu et al. |
| 10,806,927 B2 | 10/2020 | Edgerton et al. |
| 10,806,935 B2 | 10/2020 | Rao et al. |
| 11,097,122 B2 | 8/2021 | Lu |
| 11,123,312 B2 | 9/2021 | Lu et al. |
| 2001/0016266 A1 | 8/2001 | Okazaki et al. |
| 2001/0032992 A1 | 10/2001 | Wendt |
| 2002/0042814 A1 | 4/2002 | Fukasawa et al. |
| 2002/0052539 A1 | 5/2002 | Haller et al. |
| 2002/0055779 A1 | 5/2002 | Andrews |
| 2002/0083240 A1 | 6/2002 | Hoese et al. |
| 2002/0111661 A1 | 8/2002 | Cross et al. |
| 2002/0115945 A1 | 8/2002 | Herman et al. |
| 2002/0188332 A1 | 12/2002 | Lurie et al. |
| 2002/0193843 A1 | 12/2002 | Hill et al. |
| 2003/0032992 A1 | 2/2003 | Thacker et al. |
| 2003/0078633 A1 | 4/2003 | Firlik et al. |
| 2003/0093021 A1 | 5/2003 | Goffer |
| 2003/0100933 A1 | 5/2003 | Ayal et al. |
| 2003/0114894 A1 | 6/2003 | Dar et al. |
| 2003/0158583 A1 | 8/2003 | Burnett et al. |
| 2003/0220679 A1 | 11/2003 | Han |
| 2003/0233137 A1 | 12/2003 | Paul, Jr. |
| 2004/0039425 A1 | 2/2004 | Greenwood-Van Meerveld |
| 2004/0044380 A1 | 3/2004 | Bruninga et al. |
| 2004/0111118 A1 | 6/2004 | Hill et al. |
| 2004/0111126 A1 | 6/2004 | Tanagho et al. |
| 2004/0122483 A1 | 6/2004 | Nathan et al. |
| 2004/0127954 A1 | 7/2004 | McDonald, III |
| 2004/0133248 A1 | 7/2004 | Frei et al. |
| 2004/0138518 A1 | 7/2004 | Rise et al. |
| 2004/0172027 A1 | 9/2004 | Speitling et al. |
| 2004/0172097 A1 | 9/2004 | Brodard et al. |
| 2004/0181263 A1 | 9/2004 | Balzer et al. |
| 2004/0267320 A1 | 12/2004 | Taylor et al. |
| 2005/0004622 A1 | 1/2005 | Cullen et al. |
| 2005/0061315 A1 | 3/2005 | Lee et al. |
| 2005/0070982 A1 | 3/2005 | Heruth et al. |
| 2005/0075669 A1 | 4/2005 | King |
| 2005/0075678 A1 | 4/2005 | Faul |
| 2005/0090756 A1 | 4/2005 | Wolf et al. |
| 2005/0101827 A1 | 5/2005 | Delisle |
| 2005/0102007 A1 | 5/2005 | Ayal et al. |
| 2005/0113882 A1 | 5/2005 | Cameron et al. |
| 2005/0119713 A1 | 6/2005 | Whitehurst et al. |
| 2005/0125045 A1 | 6/2005 | Brighton et al. |
| 2005/0209655 A1 | 9/2005 | Bradley et al. |
| 2005/0231186 A1 | 10/2005 | Saavedra Barrera et al. |
| 2005/0246004 A1 | 11/2005 | Cameron et al. |
| 2005/0277999 A1 | 12/2005 | Strother et al. |
| 2005/0278000 A1 | 12/2005 | Strother et al. |
| 2006/0003090 A1 | 1/2006 | Rodger et al. |
| 2006/0015153 A1 | 1/2006 | Gliner et al. |
| 2006/0018360 A1 | 1/2006 | Tai et al. |
| 2006/0041225 A1 | 2/2006 | Wallace et al. |
| 2006/0041295 A1 | 2/2006 | Osypka |
| 2006/0089696 A1 | 4/2006 | Olsen et al. |
| 2006/0100671 A1 | 5/2006 | De Ridder |
| 2006/0111754 A1 | 5/2006 | Rezai et al. |
| 2006/0122678 A1 | 6/2006 | Olsen et al. |
| 2006/0142337 A1 | 6/2006 | Ikeura et al. |
| 2006/0142816 A1 | 6/2006 | Fruitman et al. |
| 2006/0142822 A1 | 6/2006 | Tulgar |
| 2006/0149333 A1 | 7/2006 | Tanagho et al. |
| 2006/0149337 A1 | 7/2006 | John |
| 2006/0189839 A1 | 8/2006 | Laniado et al. |
| 2006/0195153 A1 | 8/2006 | DiUbaldi et al. |
| 2006/0239482 A1 | 10/2006 | Hatoum |
| 2006/0241356 A1 | 10/2006 | Flaherty |
| 2006/0282127 A1 | 12/2006 | Zealear |
| 2007/0004567 A1 | 1/2007 | Shetty et al. |
| 2007/0016097 A1 | 1/2007 | Farquhar et al. |
| 2007/0016266 A1 | 1/2007 | Paul, Jr. |
| 2007/0016329 A1 | 1/2007 | Herr et al. |
| 2007/0021513 A1 | 1/2007 | Agee et al. |
| 2007/0027495 A1 | 2/2007 | Gerber |
| 2007/0047852 A1 | 3/2007 | Sharp et al. |
| 2007/0049814 A1 | 3/2007 | Muccio |
| 2007/0055337 A1 | 3/2007 | Tanrisever |
| 2007/0060954 A1 | 3/2007 | Cameron et al. |
| 2007/0060980 A1 | 3/2007 | Strother et al. |
| 2007/0067003 A1 | 3/2007 | Sanchez et al. |
| 2007/0073357 A1 | 3/2007 | Rooney et al. |
| 2007/0083240 A1 | 4/2007 | Peterson et al. |
| 2007/0100389 A1 | 5/2007 | Jaax et al. |
| 2007/0121702 A1 | 5/2007 | LaGuardia et al. |
| 2007/0121709 A1 | 5/2007 | Ittogi |
| 2007/0142874 A1 | 6/2007 | John |
| 2007/0150023 A1 | 6/2007 | Ignagni et al. |
| 2007/0156172 A1 | 7/2007 | Alvarado |
| 2007/0156179 A1 | 7/2007 | S.E. |
| 2007/0156200 A1 | 7/2007 | Kornet et al. |
| 2007/0168008 A1 | 7/2007 | Olsen |
| 2007/0179534 A1 | 8/2007 | Firlik et al. |
| 2007/0179579 A1 | 8/2007 | Feler et al. |
| 2007/0191709 A1 | 8/2007 | Swanson |
| 2007/0208381 A1 | 9/2007 | Hill et al. |
| 2007/0233204 A1 | 10/2007 | Lima et al. |
| 2007/0255372 A1 | 11/2007 | Metzler et al. |
| 2007/0265621 A1 | 11/2007 | Matthis et al. |
| 2007/0265679 A1 | 11/2007 | Bradley et al. |
| 2007/0265691 A1 | 11/2007 | Swanson |
| 2007/0276449 A1 | 11/2007 | Gunter et al. |
| 2007/0276450 A1 | 11/2007 | Meadows et al. |
| 2007/0293910 A1 | 12/2007 | Strother et al. |
| 2008/0002227 A1 | 1/2008 | Tsujimoto |
| 2008/0004674 A1 | 1/2008 | King et al. |
| 2008/0009927 A1 | 1/2008 | Vilims |
| 2008/0021513 A1 | 1/2008 | Thacker et al. |
| 2008/0027346 A1 | 1/2008 | Litt et al. |
| 2008/0046049 A1 | 2/2008 | Skubitz et al. |
| 2008/0051851 A1 | 2/2008 | Lin |
| 2008/0071325 A1 | 3/2008 | Bradley |
| 2008/0077192 A1 | 3/2008 | Harry et al. |
| 2008/0103579 A1 | 5/2008 | Gerber |
| 2008/0105185 A1 | 5/2008 | Kuhlman |
| 2008/0140152 A1 | 6/2008 | Imran et al. |
| 2008/0140162 A1 | 6/2008 | Goetz et al. |
| 2008/0140169 A1 | 6/2008 | Imran |
| 2008/0147143 A1 | 6/2008 | Popovic et al. |
| 2008/0154329 A1 | 6/2008 | Pyles et al. |
| 2008/0183224 A1 | 7/2008 | Barolat |
| 2008/0200749 A1 | 8/2008 | Zheng et al. |
| 2008/0202940 A1 | 8/2008 | Jiang et al. |
| 2008/0207985 A1 | 8/2008 | Farone |
| 2008/0208287 A1 | 8/2008 | Palermo et al. |
| 2008/0215113 A1 | 9/2008 | Pawlowicz |
| 2008/0221653 A1 | 9/2008 | Agrawal et al. |
| 2008/0224226 A1 | 9/2008 | Suzuki et al. |

(56) References Cited

U.S. PATENT DOCUMENTS

| | | |
|---|---|---|
| 2008/0228241 A1 | 9/2008 | Sachs |
| 2008/0228250 A1 | 9/2008 | Mironer |
| 2008/0234121 A1 | 9/2008 | Kim et al. |
| 2008/0234791 A1 | 9/2008 | Arle et al. |
| 2008/0279896 A1 | 11/2008 | Heinen et al. |
| 2008/0294211 A1 | 11/2008 | Moffitt |
| 2009/0012436 A1 | 1/2009 | Lanfermann et al. |
| 2009/0024997 A1 | 1/2009 | Kobayashi |
| 2009/0093854 A1 | 4/2009 | Leung et al. |
| 2009/0112281 A1 | 4/2009 | Miyazawa et al. |
| 2009/0118365 A1 | 5/2009 | Benson, III et al. |
| 2009/0131995 A1 | 5/2009 | Sloan et al. |
| 2009/0157141 A1 | 6/2009 | Chiao et al. |
| 2009/0198305 A1 | 8/2009 | Naroditsky et al. |
| 2009/0204173 A1 | 8/2009 | Zhao et al. |
| 2009/0229166 A1 | 9/2009 | Sawrie |
| 2009/0270960 A1 | 10/2009 | Zhao et al. |
| 2009/0281529 A1 | 11/2009 | Carriazo |
| 2009/0281599 A1 | 11/2009 | Thacker et al. |
| 2009/0293270 A1 | 12/2009 | Brindley et al. |
| 2009/0299166 A1 | 12/2009 | Nishida et al. |
| 2009/0299167 A1 | 12/2009 | Seymour |
| 2009/0306491 A1 | 12/2009 | Haggers |
| 2010/0004715 A1 | 1/2010 | Fahey |
| 2010/0023103 A1 | 1/2010 | Elborno |
| 2010/0029040 A1 | 2/2010 | Nomoto |
| 2010/0042193 A1 | 2/2010 | Slavin |
| 2010/0070007 A1 | 3/2010 | Parker et al. |
| 2010/0114205 A1 | 5/2010 | Donofrio et al. |
| 2010/0114239 A1 | 5/2010 | McDonald, III |
| 2010/0125313 A1 | 5/2010 | Lee et al. |
| 2010/0137238 A1 | 6/2010 | Gan et al. |
| 2010/0137938 A1 | 6/2010 | Kishawi et al. |
| 2010/0145428 A1 | 6/2010 | Cameron et al. |
| 2010/0152811 A1 | 6/2010 | Flaherty |
| 2010/0166546 A1 | 7/2010 | Mahan et al. |
| 2010/0168820 A1 | 7/2010 | Maniak et al. |
| 2010/0185253 A1 | 7/2010 | Dimarco et al. |
| 2010/0198298 A1 | 8/2010 | Glukhovsky et al. |
| 2010/0217355 A1 | 8/2010 | Tass et al. |
| 2010/0228310 A1 | 9/2010 | Shuros et al. |
| 2010/0241121 A1 | 9/2010 | Logan et al. |
| 2010/0241191 A1 | 9/2010 | Testerman et al. |
| 2010/0268299 A1 | 10/2010 | Farone |
| 2010/0274312 A1 | 10/2010 | Alataris et al. |
| 2010/0280570 A1 | 11/2010 | Sturm et al. |
| 2010/0305660 A1 | 12/2010 | Hegi et al. |
| 2010/0312304 A1 | 12/2010 | York et al. |
| 2010/0318168 A1 | 12/2010 | Bighetti |
| 2010/0331925 A1 | 12/2010 | Peterson |
| 2011/0006793 A1 | 1/2011 | Peschke et al. |
| 2011/0009919 A1 | 1/2011 | Carbunaru et al. |
| 2011/0016081 A1 | 1/2011 | Basak et al. |
| 2011/0029040 A1 | 2/2011 | Walker et al. |
| 2011/0029044 A1 | 2/2011 | Hyde et al. |
| 2011/0034277 A1 | 2/2011 | Brandes |
| 2011/0034977 A1 | 2/2011 | Janik et al. |
| 2011/0040349 A1 | 2/2011 | Graupe |
| 2011/0054567 A1 | 3/2011 | Lane et al. |
| 2011/0054568 A1 | 3/2011 | Lane et al. |
| 2011/0054570 A1 | 3/2011 | Lane |
| 2011/0054579 A1 | 3/2011 | Kumar et al. |
| 2011/0077660 A1 | 3/2011 | Janik et al. |
| 2011/0082515 A1 | 4/2011 | Libbus et al. |
| 2011/0084489 A1 | 4/2011 | Kaplan |
| 2011/0093043 A1 | 4/2011 | Torgerson et al. |
| 2011/0112601 A1 | 5/2011 | Meadows et al. |
| 2011/0125203 A1 | 5/2011 | Simon et al. |
| 2011/0130804 A1 | 6/2011 | Lin et al. |
| 2011/0152967 A1 | 6/2011 | Simon et al. |
| 2011/0166546 A1 | 7/2011 | Jaax et al. |
| 2011/0184482 A1 | 7/2011 | Eberman et al. |
| 2011/0184488 A1 | 7/2011 | De Ridder |
| 2011/0184489 A1 | 7/2011 | Nicolelis et al. |
| 2011/0202107 A1 | 8/2011 | Sunagawa et al. |
| 2011/0208265 A1 | 8/2011 | Erickson et al. |
| 2011/0213266 A1 | 9/2011 | Williams et al. |
| 2011/0218590 A1 | 9/2011 | DeGiorgio et al. |
| 2011/0218594 A1 | 9/2011 | Doron et al. |
| 2011/0224153 A1 | 9/2011 | Levitt et al. |
| 2011/0224665 A1 | 9/2011 | Crosby et al. |
| 2011/0224752 A1 | 9/2011 | Rolston et al. |
| 2011/0224753 A1 | 9/2011 | Palermo et al. |
| 2011/0224757 A1 | 9/2011 | Zdeblick et al. |
| 2011/0230101 A1 | 9/2011 | Tang et al. |
| 2011/0230701 A1 | 9/2011 | Simon et al. |
| 2011/0230702 A1 | 9/2011 | Honour |
| 2011/0231326 A1 | 9/2011 | Marino |
| 2011/0237221 A1 | 9/2011 | Prakash et al. |
| 2011/0237921 A1 | 9/2011 | Askin, III et al. |
| 2011/0245734 A1 | 10/2011 | Wagner et al. |
| 2011/0276107 A1 | 11/2011 | Simon et al. |
| 2011/0288609 A1 | 11/2011 | Tehran et al. |
| 2011/0295100 A1 | 12/2011 | Hedge et al. |
| 2012/0006793 A1 | 1/2012 | Swanson |
| 2012/0011950 A1 | 1/2012 | Kracke |
| 2012/0013041 A1 | 1/2012 | Cao et al. |
| 2012/0013126 A1 | 1/2012 | Molloy |
| 2012/0016448 A1 | 1/2012 | Lee |
| 2012/0029528 A1 | 2/2012 | MacDonald et al. |
| 2012/0035684 A1 | 2/2012 | Thompson et al. |
| 2012/0041518 A1 | 2/2012 | Kim et al. |
| 2012/0052432 A1 | 3/2012 | Matsuura |
| 2012/0059432 A1 | 3/2012 | Emborg et al. |
| 2012/0071250 A1 | 3/2012 | O'Neil et al. |
| 2012/0071950 A1 | 3/2012 | Archer |
| 2012/0083709 A1 | 4/2012 | Parker et al. |
| 2012/0101326 A1 | 4/2012 | Simon et al. |
| 2012/0109251 A1 | 5/2012 | Lebedev et al. |
| 2012/0109295 A1 | 5/2012 | Fan |
| 2012/0116476 A1 | 5/2012 | Kothandaraman |
| 2012/0123223 A1 | 5/2012 | Freeman et al. |
| 2012/0123293 A1 | 5/2012 | Shah et al. |
| 2012/0126392 A1 | 5/2012 | Kalvesten et al. |
| 2012/0136408 A1 | 5/2012 | Grill et al. |
| 2012/0165899 A1 | 6/2012 | Gliner |
| 2012/0172222 A1 | 7/2012 | Artigas Puerto |
| 2012/0172246 A1 | 7/2012 | Nguyen et al. |
| 2012/0172946 A1 | 7/2012 | Alataris et al. |
| 2012/0179222 A1 | 7/2012 | Jaax et al. |
| 2012/0185020 A1 | 7/2012 | Simon et al. |
| 2012/0197338 A1 | 8/2012 | Su et al. |
| 2012/0203055 A1 | 8/2012 | Pletnev |
| 2012/0203131 A1 | 8/2012 | DiLorenzo |
| 2012/0221073 A1 | 8/2012 | Southwell et al. |
| 2012/0232615 A1 | 9/2012 | Barolat et al. |
| 2012/0252874 A1 | 10/2012 | Feinstein et al. |
| 2012/0259380 A1 | 10/2012 | Pyles |
| 2012/0271372 A1 | 10/2012 | Osario |
| 2012/0277824 A1 | 11/2012 | Li |
| 2012/0277834 A1 | 11/2012 | Mercanzini et al. |
| 2012/0283697 A1 | 11/2012 | Kim et al. |
| 2012/0302821 A1 | 11/2012 | Burnett |
| 2012/0310305 A1 | 12/2012 | Kaula et al. |
| 2012/0310315 A1 | 12/2012 | Savage et al. |
| 2012/0330321 A1 | 12/2012 | Johnson et al. |
| 2012/0330391 A1 | 12/2012 | Bradley et al. |
| 2013/0012853 A1 | 1/2013 | Brown |
| 2013/0013041 A1 | 1/2013 | Glukhovsky et al. |
| 2013/0026640 A1 | 1/2013 | Ito et al. |
| 2013/0030312 A1 | 1/2013 | Keel et al. |
| 2013/0030319 A1 | 1/2013 | Hettrick et al. |
| 2013/0030501 A1 | 1/2013 | Feler et al. |
| 2013/0035745 A1 | 2/2013 | Ahmed et al. |
| 2013/0053734 A1 | 2/2013 | Barriskill et al. |
| 2013/0053922 A1 | 2/2013 | Ahmed et al. |
| 2013/0066392 A1 | 3/2013 | Simon et al. |
| 2013/0085317 A1 | 4/2013 | Feinstein |
| 2013/0085361 A1 | 4/2013 | Mercanzini et al. |
| 2013/0096640 A1 | 4/2013 | Possover |
| 2013/0096661 A1 | 4/2013 | Greenberg et al. |
| 2013/0096662 A1 | 4/2013 | Swanson |
| 2013/0110196 A1 | 5/2013 | Alataris et al. |
| 2013/0116751 A1 | 5/2013 | Moffitt et al. |

(56) References Cited

U.S. PATENT DOCUMENTS

| | | |
|---|---|---|
| 2013/0123568 A1 | 5/2013 | Hamilton et al. |
| 2013/0123659 A1 | 5/2013 | Bartol et al. |
| 2013/0138167 A1 | 5/2013 | Bradley et al. |
| 2013/0165991 A1 | 6/2013 | Kim et al. |
| 2013/0197408 A1 | 8/2013 | Goldfarb et al. |
| 2013/0204324 A1 | 8/2013 | Thacker et al. |
| 2013/0237948 A1 | 9/2013 | Donders et al. |
| 2013/0253222 A1 | 9/2013 | Nakao |
| 2013/0253229 A1 | 9/2013 | Sawant et al. |
| 2013/0253299 A1 | 9/2013 | Weber et al. |
| 2013/0253611 A1 | 9/2013 | Lee et al. |
| 2013/0268016 A1 | 10/2013 | Xi et al. |
| 2013/0268021 A1 | 10/2013 | Moffitt |
| 2013/0281890 A1 | 10/2013 | Mishelevich |
| 2013/0289446 A1 | 10/2013 | Stone et al. |
| 2013/0289650 A1 | 10/2013 | Karlsson et al. |
| 2013/0289664 A1 | 10/2013 | Johanek |
| 2013/0289667 A1 | 10/2013 | Wacnik et al. |
| 2013/0296965 A1 | 11/2013 | Mokelke et al. |
| 2013/0303873 A1 | 11/2013 | Voros et al. |
| 2013/0304159 A1 | 11/2013 | Simon et al. |
| 2013/0310211 A1 | 11/2013 | Wilton et al. |
| 2013/0310911 A1 | 11/2013 | Tai et al. |
| 2014/0005753 A1 | 1/2014 | Carbunaru |
| 2014/0031893 A1 | 1/2014 | Walker et al. |
| 2014/0046407 A1 | 2/2014 | Ben-Ezra et al. |
| 2014/0058292 A1 | 2/2014 | Alford et al. |
| 2014/0058490 A1 | 2/2014 | DiMarco |
| 2014/0066950 A1 | 3/2014 | MacDonald et al. |
| 2014/0067007 A1 | 3/2014 | Drees et al. |
| 2014/0067354 A1 | 3/2014 | Kaula et al. |
| 2014/0074190 A1 | 3/2014 | Griffith |
| 2014/0081011 A1 | 3/2014 | Vaught et al. |
| 2014/0081071 A1 | 3/2014 | Simon et al. |
| 2014/0088674 A1 | 3/2014 | Bradley |
| 2014/0100633 A1 | 4/2014 | Mann et al. |
| 2014/0107397 A1 | 4/2014 | Simon et al. |
| 2014/0107398 A1 | 4/2014 | Simon et al. |
| 2014/0114374 A1 | 4/2014 | Rooney et al. |
| 2014/0163640 A1 | 6/2014 | Edgerton et al. |
| 2014/0180361 A1 | 6/2014 | Burdick et al. |
| 2014/0213842 A1 | 7/2014 | Simon et al. |
| 2014/0228905 A1* | 8/2014 | Bolea ............... A61F 5/56 607/42 |
| 2014/0236257 A1 | 8/2014 | Parker et al. |
| 2014/0243923 A1 | 8/2014 | Doan et al. |
| 2014/0277271 A1 | 9/2014 | Chan et al. |
| 2014/0296752 A1 | 10/2014 | Edgerton et al. |
| 2014/0303901 A1 | 10/2014 | Sadeh |
| 2014/0316484 A1 | 10/2014 | Edgerton et al. |
| 2014/0316503 A1 | 10/2014 | Tai et al. |
| 2014/0324118 A1 | 10/2014 | Simon et al. |
| 2014/0330067 A1 | 11/2014 | Jordan |
| 2014/0330335 A1 | 11/2014 | Errico et al. |
| 2014/0336722 A1 | 11/2014 | Rocon de Lima et al. |
| 2014/0357936 A1 | 12/2014 | Simon et al. |
| 2015/0005840 A1 | 1/2015 | Pal et al. |
| 2015/0065559 A1 | 3/2015 | Feinstein et al. |
| 2015/0066111 A1 | 3/2015 | Blum et al. |
| 2015/0165226 A1 | 6/2015 | Simon et al. |
| 2015/0182784 A1 | 7/2015 | Barriskill et al. |
| 2015/0190634 A1 | 7/2015 | Rezai et al. |
| 2015/0196231 A1 | 7/2015 | Ziaie et al. |
| 2015/0217120 A1 | 8/2015 | Nandra et al. |
| 2015/0231396 A1 | 8/2015 | Burdick et al. |
| 2015/0265830 A1 | 9/2015 | Simon et al. |
| 2015/0328462 A1 | 11/2015 | Griffith |
| 2016/0001096 A1 | 1/2016 | Mishelevich |
| 2016/0030737 A1 | 2/2016 | Gerasimenko et al. |
| 2016/0030748 A1 | 2/2016 | Edgerton et al. |
| 2016/0030750 A1 | 2/2016 | Bokil et al. |
| 2016/0045727 A1 | 2/2016 | Rezai et al. |
| 2016/0045731 A1 | 2/2016 | Simon et al. |
| 2016/0074663 A1 | 3/2016 | De Ridder |
| 2016/0121109 A1 | 5/2016 | Edgerton et al. |
| 2016/0121114 A1 | 5/2016 | Simon et al. |
| 2016/0121116 A1 | 5/2016 | Simon et al. |
| 2016/0121121 A1 | 5/2016 | Mashiach |
| 2016/0143588 A1 | 5/2016 | Hoitink et al. |
| 2016/0157389 A1 | 6/2016 | Hwang |
| 2016/0175586 A1 | 6/2016 | Edgerton et al. |
| 2016/0220813 A1 | 8/2016 | Edgerton et al. |
| 2016/0235977 A1 | 8/2016 | Lu et al. |
| 2016/0271413 A1 | 9/2016 | Vallejo et al. |
| 2016/0279418 A1 | 9/2016 | Courtine et al. |
| 2016/0310739 A1 | 10/2016 | Burdick et al. |
| 2017/0007320 A1 | 1/2017 | Levin et al. |
| 2017/0007831 A1 | 1/2017 | Edgerton et al. |
| 2017/0128729 A1 | 5/2017 | Netoff et al. |
| 2017/0157389 A1 | 6/2017 | Tai et al. |
| 2017/0157396 A1 | 6/2017 | Dixon et al. |
| 2017/0161454 A1 | 6/2017 | Grill et al. |
| 2017/0165497 A1 | 6/2017 | Lu |
| 2017/0173326 A1 | 6/2017 | Bloch et al. |
| 2017/0246450 A1 | 8/2017 | Liu et al. |
| 2017/0246452 A1 | 8/2017 | Liu et al. |
| 2017/0266455 A1 | 9/2017 | Steinke |
| 2017/0274209 A1 | 9/2017 | Edgerton et al. |
| 2017/0296837 A1 | 10/2017 | Jin |
| 2017/0354819 A1 | 12/2017 | Bloch et al. |
| 2017/0361093 A1 | 12/2017 | Yoo |
| 2018/0056078 A1 | 3/2018 | Kashyap et al. |
| 2018/0085583 A1 | 3/2018 | Zhang et al. |
| 2018/0104479 A1 | 4/2018 | Grill et al. |
| 2018/0110992 A1 | 4/2018 | Parramon et al. |
| 2018/0125416 A1 | 5/2018 | Schwarz et al. |
| 2018/0178008 A1 | 6/2018 | Bouton et al. |
| 2018/0185642 A1 | 7/2018 | Lu |
| 2018/0185648 A1 | 7/2018 | Nandra et al. |
| 2018/0193655 A1 | 7/2018 | Zhang et al. |
| 2018/0229037 A1 | 8/2018 | Edgerton et al. |
| 2018/0229038 A1 | 8/2018 | Burdick et al. |
| 2018/0236240 A1* | 8/2018 | Harkema ............ A61B 5/0031 |
| 2018/0256906 A1 | 9/2018 | Pivonka et al. |
| 2018/0280693 A1 | 10/2018 | Edgerton et al. |
| 2018/0353755 A1 | 12/2018 | Edgerton et al. |
| 2018/0361146 A1 | 12/2018 | Gerasimenko et al. |
| 2019/0022371 A1 | 1/2019 | Chang et al. |
| 2019/0033622 A1 | 1/2019 | Olgun et al. |
| 2019/0160294 A1 | 5/2019 | Peterson et al. |
| 2019/0167987 A1 | 6/2019 | Lu et al. |
| 2019/0192864 A1* | 6/2019 | Koop ................... A61N 1/3756 |
| 2019/0247650 A1 | 8/2019 | Tran |
| 2019/0269917 A1 | 9/2019 | Courtine et al. |
| 2019/0381313 A1 | 12/2019 | Lu |
| 2020/0155865 A1 | 5/2020 | Lu |
| 2020/0228901 A1* | 7/2020 | Baek .................. H04R 25/405 |
| 2021/0069052 A1 | 3/2021 | Burke |
| 2021/0187278 A1 | 6/2021 | Lu |
| 2021/0236837 A1 | 8/2021 | Lu |
| 2021/0378991 A1 | 12/2021 | Lu |

FOREIGN PATENT DOCUMENTS

| | | |
|---|---|---|
| CA | 2864473 A1 | 5/2013 |
| CA | 2823592 A1 | 11/2021 |
| CN | 101227940 A | 7/2008 |
| CN | 103263727 A | 8/2013 |
| CN | 104307098 A | 1/2015 |
| EP | 0630987 A1 | 12/1994 |
| EP | 2130326 A1 | 12/2009 |
| EP | 2141851 A2 | 1/2010 |
| EP | 2160127 A1 | 3/2010 |
| EP | 2178319 A1 | 4/2010 |
| EP | 2192897 A1 | 6/2010 |
| EP | 2226114 A1 | 9/2010 |
| EP | 2258496 A1 | 12/2010 |
| EP | 2361631 A1 | 8/2011 |
| EP | 2368401 A1 | 9/2011 |
| EP | 2387467 A1 | 11/2011 |
| EP | 2396995 A1 | 12/2011 |
| EP | 2397788 A1 | 12/2011 |
| EP | 2445990 A2 | 5/2012 |
| EP | 2471518 A2 | 7/2012 |

(56) References Cited

FOREIGN PATENT DOCUMENTS

| | | |
|---|---|---|
| EP | 2475283 A1 | 7/2012 |
| EP | 2486897 A2 | 8/2012 |
| EP | 2626051 A1 | 8/2013 |
| EP | 2628502 A1 | 8/2013 |
| EP | 2661307 A2 | 11/2013 |
| EP | 2688642 A2 | 1/2014 |
| EP | 2810689 A1 | 12/2014 |
| EP | 2810690 A1 | 12/2014 |
| EP | 2868343 A1 | 5/2015 |
| EP | 2966422 A1 | 1/2016 |
| EP | 2968940 A1 | 1/2016 |
| EP | 3184145 A1 | 6/2017 |
| EP | 3323468 A1 | 5/2018 |
| EP | 3328481 A1 | 6/2018 |
| EP | 3527258 A1 | 8/2019 |
| JP | H0326620 A | 2/1991 |
| JP | 3184145 B2 | 7/2001 |
| JP | 2002200178 A | 7/2002 |
| JP | 2004065529 A | 3/2004 |
| JP | 2007526798 A | 9/2007 |
| JP | 2008067917 A | 3/2008 |
| JP | 2008543429 A | 12/2008 |
| JP | 2014514043 A | 6/2014 |
| JP | 6132856 A | 3/2015 |
| JP | 2016506255 A | 3/2016 |
| JP | 2017104685 A | 6/2017 |
| JP | 2017525509 A | 9/2017 |
| JP | 2018524113 A | 8/2018 |
| RU | 2130326 C1 | 5/1999 |
| RU | 2141851 C1 | 11/1999 |
| RU | 2160127 C1 | 12/2000 |
| RU | 2178319 C2 | 1/2002 |
| RU | 2192897 C2 | 11/2002 |
| RU | 2001102533 | 11/2002 |
| RU | 2226114 C1 | 3/2004 |
| RU | 2258496 C2 | 8/2005 |
| RU | 2361631 C2 | 7/2009 |
| RU | 2368401 C1 | 9/2009 |
| RU | 2387467 C1 | 4/2010 |
| RU | 2396995 C2 | 8/2010 |
| RU | 2397788 C2 | 8/2010 |
| RU | 2445990 C1 | 3/2012 |
| RU | 2471518 C2 | 1/2013 |
| RU | 2475283 C2 | 2/2013 |
| RU | 2661307 C1 | 7/2018 |
| WO | WO 1997047357 A1 | 12/1997 |
| WO | 0234331 A1 | 5/2002 |
| WO | WO 2002092165 A1 | 11/2002 |
| WO | WO 2003005887 A2 | 1/2003 |
| WO | WO 2003026735 A2 | 4/2003 |
| WO | WO 2003092795 A1 | 11/2003 |
| WO | WO 2004087116 A2 | 10/2004 |
| WO | 2005002663 A2 | 1/2005 |
| WO | WO 2005002663 A2 | 1/2005 |
| WO | WO 2005051306 A2 | 6/2005 |
| WO | WO 2005065768 A1 | 7/2005 |
| WO | WO 2005087307 A2 | 9/2005 |
| WO | WO 2006138069 A1 | 12/2006 |
| WO | WO 2007007058 A1 | 1/2007 |
| WO | WO 2007012114 A1 | 2/2007 |
| WO | WO 2007047852 A1 | 4/2007 |
| WO | WO 2007081764 A2 | 7/2007 |
| WO | WO 2007107831 A2 | 9/2007 |
| WO | WO 2008070807 A3 | 6/2008 |
| WO | WO 2008075294 A1 | 6/2008 |
| WO | WO 2008092785 A1 | 8/2008 |
| WO | WO 2008109862 A2 | 9/2008 |
| WO | WO 2008121891 A1 | 10/2008 |
| WO | WO 2009042217 A1 | 4/2009 |
| WO | WO 2009111142 A2 | 9/2009 |
| WO | WO 2010021977 A1 | 2/2010 |
| WO | WO 2010055421 A1 | 5/2010 |
| WO | WO 2010114998 A1 | 10/2010 |
| WO | WO 2010124128 A1 | 10/2010 |
| WO | WO 2011005607 A1 | 1/2011 |
| WO | WO 2011136875 A1 | 11/2011 |
| WO | WO 2012075195 A1 | 6/2012 |
| WO | WO 2012080964 A1 | 6/2012 |
| WO | WO 2012094346 A2 | 7/2012 |
| WO | WO 2012100260 A2 | 7/2012 |
| WO | WO 2012129574 A2 | 9/2012 |
| WO | WO 2013071307 A1 | 5/2013 |
| WO | WO 2013071309 A1 | 5/2013 |
| WO | WO 2013152124 A1 | 10/2013 |
| WO | WO 2013179230 A1 | 12/2013 |
| WO | WO 2013188965 A1 | 12/2013 |
| WO | WO 2014005075 A1 | 1/2014 |
| WO | WO 2014031142 A1 | 2/2014 |
| WO | WO 2014089299 A2 | 6/2014 |
| WO | WO 2014144785 A1 | 9/2014 |
| WO | WO 2014149895 A1 | 9/2014 |
| WO | WO 2014205356 A2 | 12/2014 |
| WO | WO 2014209877 A1 | 12/2014 |
| WO | WO 2015000800 A1 | 1/2015 |
| WO | WO 2015048563 A2 | 4/2015 |
| WO | WO 2015063127 A1 | 5/2015 |
| WO | WO 2015106286 A1 | 7/2015 |
| WO | WO 2016029159 A2 | 2/2016 |
| WO | WO 2016033369 A1 | 3/2016 |
| WO | WO 2016033372 A1 | 3/2016 |
| WO | WO 2016064761 A1 | 4/2016 |
| WO | 2016110804 A1 | 7/2016 |
| WO | WO 2016110804 A1 | 7/2016 |
| WO | WO 2016112398 A1 | 7/2016 |
| WO | WO 2016172239 A1 | 10/2016 |
| WO | WO 2017011410 A1 | 1/2017 |
| WO | WO 2017024276 A1 | 2/2017 |
| WO | WO 2017035512 A1 | 3/2017 |
| WO | WO 2017044904 A1 | 3/2017 |
| WO | 2017058913 A1 | 4/2017 |
| WO | 2017062508 A1 | 4/2017 |
| WO | WO 2017058913 A1 | 4/2017 |
| WO | WO 2017062508 A1 | 4/2017 |
| WO | WO 2017146659 A1 | 8/2017 |
| WO | WO 2018039296 A2 | 3/2018 |
| WO | WO 2018106843 A1 | 6/2018 |
| WO | WO 2018160531 A1 | 8/2018 |
| WO | WO 2018217791 A1 | 11/2018 |
| WO | WO 2012050200 A1 | 4/2019 |
| WO | WO 2019211314 A1 | 11/2019 |
| WO | WO 2020041502 A1 | 2/2020 |
| WO | WO 2020416331 A1 | 2/2020 |
| WO | WO 2020236946 A1 | 11/2020 |

OTHER PUBLICATIONS

Minassian, K. et al., "Stepping-like movements in humans with complete spinal cord injury induced by epidural stimulation of the lumbar cord: electromyographic study of compound muscle action potentials," Spinal Cord, vol. 42, No. 7, Jul. 2004, Published Online May 4, 2004, 16 pages.
Courtine, G. et al., "Transformation of nonfunctional spinal circuits into functional states after the loss of brain input," Nature Neuroscience, vol. 12, No. 10, Oct. 2009, Published Online Sep. 20, 2009, 12 pages.
Capogrosso, M. et al., "A Computational Model for Epidural Electrical Stimulation of Spinal Sensorimotor Circuits," Journal of Neuroscience, vol. 33, No. 49, Dec. 4, 2013, 15 pages.
Levine, A. et al., "Identification of cellular node for motor control pathways," Nature Neuroscience, vol. 17, No. 4, Apr. 2014, Available Online Mar. 9, 2014, 22 pages.
Angeli, C. et al., "Altering spinal cord excitability enables voluntary movements after chronic complete paralysis in humans," Brain: A Journal of Neurology, vol. 137, No. 5, May 1, 2014, Published Online Apr. 8, 2014, 16 pages.
Wenger, N. et al., "Closed-loop neuromodulation of spinal sensorimotor circuits controls refined locomotion after complete spinal cord injury," Science Translational Medicine, vol. 6, No. 255, Sep. 24, 2014, 12 pages.
Danner, S. et al., "Human spinal locomotor control is based on flexibly organized burst generators," Brain: A Journal of Neurology,

(56) References Cited

OTHER PUBLICATIONS vol. 138, No. 3, Mar. 1, 2015, Published Online Jan. 12, 2015, 12 pages.
Moraud, E. et al., "Mechanisms Underlying the Neuromodulation of Spinal Circuits for Correcting Gait and Balance Deficits after Spinal Cord Injury," Neuron, vol. 89, No. 4, Feb. 17, 2016, Available Online Feb. 4, 2016, 16 pages.
Capogrosso, M. et al., "A Brain-Spinal Interface Alleviating Gait Deficits after Spinal Cord Injury in Primates," Nature, vol. 539, No. 7628, Nov. 10, 2016, 39 pages.
Abernethy, J. et al., "Competing in the Dark: An Efficient Algorithm for Bandit Linear Optimization", Conference on Learning Theory, (2008), 13 pages.
Ada, L. et al., "Mechanically assisted walking with body weight support results in more independent walking than assisted overground walking in non-ambulatory patients early after stroke: a systematic review," Journal of Physiotherapy, vol. 56, No. 3, (Sep. 2010), 9 pages.
Alto, L. et al., "Chemotropic Guidance Facilitates Axonal Regeneration and Synapse Formation after Spinal Cord Injury," Nature Neuroscience, vol. 12, No. 9, Published Online Aug. 2, 2009, (Sep. 2009), 22 pages.
Angeli, C. et al., "Altering spinal cord excitability enables voluntary movements after chronic complete paralysis in humans," Brain, vol. 137, No. 5, May 2014, Available Online Apr. 8, 2014, 16 pages.
Anderson, K., "Targeting Recovery: Priorities of the Spinal Cord-Injured Population," Journal of Neurotrauma, vol. 21, No. 10, (Oct. 2004), 13 pages.
Auer, P. et al., "Finite-time Analysis of the Multiarmed Bandit Problem", Machine Learning, vol. 47, No. 2, (2002), pp. 235-256.
Auer, P. "Using Confidence Bounds for Exploitation-Exploration Trade-offs", Journal of Machine Learning Research, vol. 3, (2002), pp. 397-422.
Azimi, J. et al., "Batch Bayesian Optimization via Simulation Matching", In Advances in Neural Information Processing Systems (NIPS), (2010), 9 pages.
Azimi, J. et al., "Hybrid Batch Bayesian Optimization", In Proceedings of the 29th International Conference on Machine Learning, (2012), 12 pages.
Azimi, J. et al., "Batch Active Learning via Coordinated Matching", In Proceedings of the 29th International Conference on Machine Learning, (2012), 8 pages.
Barbeau, H. et al., "Recovery of locomotion after chronic spinalization in the adult cat", Brain Research, vol. 412, No. 1, (May 26, 1987), 12 pages.
Bareyre, F. et al., "The injured spinal cord spontaneously forms a new intraspinal circuit in adult rats," Nature Neuroscience, vol. 7, No. 3, Published Online Feb. 15, 2004, (Mar. 2004), 9 pages.
Basso, D. M. et al., "MASCIS Evaluation of Open Field Locomotor Scores: Effects of Experience and Teamwork on Reliability," Journal of Neurotrauma, vol. 13, No. 7, (Jul. 1996), 17 pages.
Brochu, et al., "A Tutorial on Bayesian Optimization of Expensive Cost Functions, with Application to Active User Modeling and Hierarchical Reinforcement Learning", In TR-2009-23, UBC, (2009), 49 pages.
Brosamle, C. et al., "Cells of Origin, Course, and Termination Patterns of the Ventral, Uncrossed Component of the Mature Rat Corticospinal Tract," The Journal of Comparative Neurology, vol. 386, No. 2, (Sep. 22, 1997), 11 pages.
Bubeck, S. et al., "Online Optimization in X-Armed Bandits", Advances in Neural Information Processing Systems (NIPS), (2008), 8 pages.
Bubeck, S. et al., "Pure Exploration in Finitely-Armed and Continuous-Armed Bandits problems" In ALT, (2009), 35 pages.
Burke, R., "Group la Synaptic Input to Fast and Slow Twitch Motor Units of Cat Triceps Surae", The Journal of Physiology, vol. 196, vol. 3, (Jun. 1, 1968), 26 pages.
Cai, L. et al., "Implications of Assist-As-Needed Robotic Step Training after a Complete Spinal Cord Injury on Intrinsic Strategies of Motor Learning", The Journal of Neuroscience, vol. 26, No. 41, (Oct. 11, 2006), 5 pages.
Capogrosso, M. et al., A Computational Model for Epidural Electrical Stimulation of Spinal Sensorimotor Circuits, Journal of Neuroscience, vol. 33, No. 49, Dec. 4, 2013, pp. 19326-19340.
Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, (Mar. 15, 2004), 11 pages.
Colgate, E. et al., "An Analysis of Contact Instability in Terms of Passive Physical Equivalents," Proceedings of the 1989 IEEE International Conference on Robotics and Automation, Scottsdale, Arizona, (May 14, 1989), 6 pages.
Courtine, G. et al., "Can experiments in nonhuman primates expedite the translation of treatments for spinal cord injury in humans?", Nature Medicine, vol. 13, No. 5, (May 2007), 13 pages.
Courtine, G. et al., "Recovery of supraspinal control of stepping via indirect propriospinal relay connections after spinal cord injury," Nature Medicine, vol. 14, No. 1, (Jan. 6, 2008), 6 pages.
Courtine, G. et al., "Transformation of nonfunctional spinal circuits into functional states after the loss of brain input," Nature Neuroscience, vol. 12, No. 10, Published Online Sep. 20, 2009, (Oct. 2009), 12 pages.
Cowley, K. et al., "Propriospinal neurons are sufficient for bulbospinal transmission of the locomotor command signal in the neonatal rat spinal cord," The Journal of Physiology, vol. 586, No. 6, Published Online Jan. 31, 2008, (Mar. 15, 2008), 13 pages.
Dani, V. et al., "Stochastic Linear Optimization Under Bandit Feedback", In Proceedings of the 21st Annual Conference on Learning Theory (COLT), (2008), 15 pages.
Danner, S. M. et al., "Body Position Influences Which neural structures are recruited by lumbar transcutaneous spinal cord stimulation", PLoS One, vol. 11, No. 1, (2016), 13 pages.
Danner, S. et al., "Human spinal locomotor control is based on flexibly organized burst generators," Brain, vol. 138, No. 3, Available Online Jan. 12, 2015, Mar. 2015, 12 pages.
Dimitrijevic, M. M. et al., "Evidence for a Spinal Central Pattern Generator in Humans", Annals New York Academy Sciences, vol. 860, (1998), pp. 360-376.
Dimitrijevic, M. M. et al., "Clinical Elements for the Neuromuscular Stimulation and Functional Electrical Stimulation protocols in the Practice of Neurorehabilitation", Artificial Organs, vol. 26, No. 3, (2002), pp. 256-259.
Dimitrijevic, M. R. et al., "Electrophysiological characteristics of H-reflexes elicited by percutaneous stimulation of the cauda equina", Abstract No. 4927, 34th Annual Meeting of the Society for Neuroscience, San Diego, CA (2004).
Drew, T. et al., "Cortical mechanisms involved in visuomotor coordination during precision walking," Brain Research Reviews, vol. 57, No. 1, Published Online Aug. 22, 2007, (Jan. 2007), 13 pages.
Duschau-Wicke, A. et al., "Patient-cooperative control increases active participation of individuals with SCI during robot-aided gait training," Journal of NeuroEngineering and Rehabilitation, vol. 7, No. 43, (Sep. 10, 2010), 13 pages.
Edgerton, V. et al., "Training Locomotor Networks," Brain Research Reviews, vol. 57, Published Online Sep. 16, 2007, (Jan. 2008), 25 pages.
Edgerton, V. et al., "Robotic Training and Spinal Cord Plasticity," Brain Research Bulletin, vol. 78, No. 1, Published Online Nov. 14, 2008, (Jan. 15, 2009), 19 pages.
Fleshman, J. et al., "Electronic Architecture of Type-Identified a-Motoneurons in the Cat Spinal Cord," Journal of Neurophysiology, vol. 60, No. 1, (Jul. 1, 1988), 26 pages.
Frey, M. et al., "A Novel Mechatronic Body Weight Support System," IEEE Transactions on Neural Systems and Rehabilitation Engineering, vol. 14, No. 3, (Sep. 18, 2006), 11 pages.
Fuentes, R. et al., "Spinal Cord Stimulation Restores Locomotion in Animal Models of Parkinson's Disease," Science, vol. 323, No. 5921, (Mar. 20, 2009), 14 pages.

(56) References Cited

OTHER PUBLICATIONS

Ganley, K. J. et al., "Epidural Spinal Cord Stimulation Improves Locomoter Performance in Low Asia C, Wheelchair-Dependent, Spinal Cord-Injured Individuals: Insights from Metabolic Response", Top. Spinal Cord Inj. Rehabil, vol. 11, No. 2, (2005), pp. 60-63.
Gerasimenko, Yu. P. et al., "Control of Locomotor Activity in Humans and Animals in the Absence of Supraspinal Influences", Neuroscience and Behavioral Physiology, vol. 32, No. 4, (2002), pp. 417-423.
Gerasimenko, Yu. P. et al., "Noninvasive Reactivation of Motor Descending Control after Paralysis", Journal of Neurotrauma, vol. 32, (2015), 13 pages.
Gilja, V. et al., "A high-performance neural prosthesis enabled by control algorithm design," Nature Neuroscience, vol. 15, No. 12, Published Online Nov. 18, 2012, (Dec. 2012), 56 pages.
Gittins, J. C., "Bandit Processes and Dynamic Allocation Indices", Journal of the Royal Statistical Society B, vol. 41, No. 2, (1979), pp. 148-177.
Guyatt, G. H. et al., "The 6-minute walk: a new measure of exercise capacity in patients with chronic heart failure," Canadian Medical Association Journal, vol. 132, No. 8, (Apr. 15, 1985), 5 pages.
Hagglund, M. et al., "Activation of groups of excitatory neurons in the mammalian spinal cord or hindbrain evokes locomotion," Nature Neuroscience, vol. 13, No. 2, Published Online Jan. 17, 2010, (Feb. 2010), 8 pages.
Harrison, P. et al., "Individual Excitatory Post-Synaptic Potentials Due to Muscle Spindle la Afferents in Cat Triceps Surae Motoneurones," The Journal of Physiology, vol. 312, No. 1, (Mar. 1981), pp. 455-470.
Harkema, S. et al., "Human Lumbosacral Spinal Cord Interprets Loading During Stepping," Journal of Neurophysiology, vol. 77, No. 2, (Feb. 1, 1997), 15 pages.
Harkema, S. et al., "Effect of Epidural stimulation of the lumbosacral spinal cord on voluntary movement, standing, and assisted stepping after motor complete paraplegia: a case study," Lancet, vol. 377, No. 9781, Jun. 4, 2011, Available Online May 19, 2011, 17 pages.
Hashtrudi-Zaad, K. et al., "On the Use of Local Force Feedback for Transparent Teleoperation," Proceedings of the 1999 IEEE International Conference on Robotics and Automation, (May 10, 1999), 7 pages.
Hennig, P. et al., "Entropy search for information-efficient global optimization" Journal of Machine Learning Research (JMLR), vol. 13, (Jun. 2012), pp. 1809-1837.
Herman, R. et al., "Spinal cord stimulation facilitates functional walking in a chronic, incomplete spinal cord injured," Spinal Cord, vol. 40, No. 2, (2002), 4 pages.
Hidler, J. et al., "ZeroG: Overground gait and balance training system," Journal of Rehabilitation Research & Development, vol. 48, No. 4, Available as Early as Jan. 1, 2011, (2011), 12 pages.
Hines, M. L. et al., "The Neuron Simulation Environment," Neural Computation, vol. 9, No. 6, (Aug. 15, 1997), 26 pages.
Hofstoetter, U. S. et al., "Modification of Reflex Responses to Lumbar Posterior Root Stimulation by Motor Tasks in Healthy Subjects", Artificial Organs, vol. 32, No. 8, (2008), pp. 644-648.
Hofstoetter, U. S. et al., "Model of spinal cord reflex circuits in humans: Stimulation frequency-dependence of segmental activities and their interactions", Second Congress International Society of Intraoperative Neurophysiology (ISIN), Dubrovnik, Croatia, (2009), 149 pages.
Hofstoetter, U. S. et al., "Effects of transcutaneous spinal cord stimulation on voluntary locomotor activity in an incomplete spinal cord injured individual", Biomed Tech, vol. 58 (Suppl. 1), (2013), 3 pages.
Hofstoetter, U. S. et al., "Modification of spasticity by transcutaneous spinal cord stimulation in individuals with incomplete spinal cord injury", The Journal of Spinal Cord Medicine, vol. 37, No. 2, (2014), pp. 202-211.
Ivanenko, Y. P. et al., "Temporal Components of the Motor Patterns Expressed by the Human Spinal Cord Reflect Foot Kinematics," Journal of Neurophysiology, vol. 90, No. 5, Nov. 2003, Published Online Jul. 9, 2003, (2003), 11 pages.
Jarosiewicz, B. et al., "Supplementary Materials for Virtual typing by people with tetraplegia using a self-calibrating intracortical brain-computer interface," Science Translational Medicine, vol. 7, No. 313, (Nov. 11, 2015), 26 pages.
Jarosiewicz, B. et al., "Virtual typing by people with tetraplegia using a self-calibrating intracortical brain-computer interface," Science Translational Medicine, vol. 7, No. 313, (Nov. 11, 2015), 11 pages.
Jilge, B. et al., "Initiating extension of the lower limbs in subjects with complete spinal cord injury by epidural lumbar cord stimulation", Exp Brain Res., vol. 154, (2004), pp. 308-326.
Johnson, W. L. et al., "Application of a Rat Hindlimb Model: A Prediction of Force Spaces Reachable Through Stimulation of Nerve Fascicles," IEEE Transactions on Bio-Medical Engineering, vol. 58, No. 12, Available Online Jan. 17, 2011, (Dec. 2011), 22 pages.
Jones, K. E. et al., "Computer Simulation of the Responses of Human Motoneurons to Composite 1A EPSPS: Effects of Background Firing Rate," The Journal of Physiology, vol. 77, No. 1, (1997), 16 pages.
Jones, D. R. et al., "Efficient Global Optimization of Expensive Black-Box Functions", Journal of Global Optimization, vol. 13, (1998), pp. 455-492.
Kakulas, B., "A Review of the Neuropathology of Human Spinal Cord Injury with Emphasis on Special Features," Proceedings of the Donald Munro Memorial Lecture at the American Paraplegia Society 44th Annual Conference, Las Vegas, Nevada, (Sep. 9, 1998), 6 pages.
Kirkwood, P., "Neuronal Control of Locomotion: From Mollusc to Man—G.N. Orlovsky, T.G. Deliagina and S. Grillner. Oxford University Press, Oxford, 1999. ISBN 0198524056 (Hbk), 322 pp.," Clinical Neurophysiology, vol. 111, No. 8, Published Online Jul. 17, 2000, (Aug. 1, 2000), 2 pages.
Kleinberg, R. et al., "Multi-armed bandits in metric spaces", In STOC, Computer and Automation Research Institute of the Hungarian Academy of Sciences, Budapest, Hungary, (2008), pp. 681-690.
Kocsis, L. et al. "Bandit Based Monte-Carlo Planning", European Conference on Machine Learning, Springer, Berlin, Heidelberg, (Sep. 2006), pp. 282-293.
Krassioukov, A. et al., "A Systematic Review of the Management of Autonomic Dysreflexia Following Spinal Cord Injury," Archives of Physical Medicine and Rehabilitation, vol. 90, No. 4, (Apr. 2009), 27 pages.
Krassioukov, A. et al., "A Systematic Review of the Management of Orthostatic Hypotension Following Spinal Cord Injury," Archives of Physical Medicine and Rehabilitation, vol. 90, No. 5, (May 2009), 22 pages.
Krause, A. et al., "Near-optimal Nonmyopic Value of Information in Graphical Models", In UAI, (2005), 8 pages.
Krause, A. et al. "Near-Optimal Sensor Placements in Gaussian Processes: Theory, Efficient Algorithms and Empirical Studies", Journal of Machine Learning Research (JMLR), vol. 9, (Feb. 2008), pp. 235-284.
Krause, A. et al. "Contextual Gaussian Process Bandit Optimization", In Advances in Neural Information Processing Systems (NIPS), (2011), 9 pages.
Kwakkel, G. et al., "Effects of Robot-assisted therapy on upper limb recovery after stroke: A Systematic Review," Neurorehabilitation and Neural Repair, vol. 22, No. 2, Published Online Sep. 17, 2007, (Mar. 2008), 17 pages.
Ladenbauer, J. et al., "Stimulation of the human lumbar spinal cord with implanted and surface electrodes: a computer simulation study", IEEE Transactions on Neural Systems and Rehabilitation Engineering, vol. 18, No. 6, (2010), pp. 637-645.
Lavrov, I. et al., "Epidural Stimulation Induced Modulation of Spinal Locomotor Networks in Adult Spinal Rats," Journal of Neuroscience, vol. 28, No. 23, (Jun. 4, 2008), 8 pages.
Liu, J. et al., "Stimulation of the Parapyramidal Region of the Neonatal Rat Brain Stem Produces Locomotor-Like Activity Involv-

(56) References Cited

OTHER PUBLICATIONS ing Spinal 5-HT$_7$ and 5-HT$_{2A}$ Receptors", Journal of Neurophysiology, vol. 94, No. 2, Published Online May 4, 2005, (Aug. 1, 2005), 13 pages.
Lizotte, D. et al., "Automatic gait optimization with Gaussian process regression", In IJCAI, (2007), pp. 944-949.
Lovely, R. et al., "Effects of Training on the Recovery of Full-Weight-Bearing Stepping in the Adult Spinal Cat," Experimental Neurology, vol. 92, No. 2, (May 1986), 15 pages.
Lozano, A. et al., "Probing and Regulating Dysfunctional Circuits Using Deep Brain Stimulation," Neuron, vol. 77, No. 3, (Feb. 6, 2013), 19 pages.
McIntyre, C. C. et al., "Modeling the Excitability of Mammalian Nerve Fibers: Influence of Afterpotentials on the Recovery Cycle," Journal of Neurophysiology, vol. 87, No. 2, (Feb. 2002), 12 pages.
Minassian, K. et al., "Stepping-like movements in humans with complete spinal cord injury induced by epidural stimulation of the lumbar cord: electromyographic study of compound muscle action potentials", Spinal Cord, vol. 42, (2004), pp. 401-416.
Minassian, K. et al., "Peripheral and Central Afferent Input to the Lumbar Cord", Biocybernetics and Biomedical Engineering, vol. 25, No. 3, (2005), pp. 11-29.
Minassian, K. et al., "Human lumbar cord circuitries can be activated by extrinsic tonic input to generate locomotor-like activity", Human Movement Science, vol. 26, No. 2, (2007), pp. 275-295.
Minassian, K. et al., "Posterior root-muscle reflex", Second Congress International Society of Intraoperative Neurophysiology (ISIN), Dubrovnik, Croatia, (2009), pp. 77-80.
Minassian, K. et al., "Transcutaneous stimulation of the human lumbar spinal cord: Facilitating locomotor output in spinal cord injury", Society for Neuroscience, Conference Proceedings, Neuroscience 2010, San Diego, CA, Abstract Viewer/ Itinerary Planner No. 286. 19, Abstract & Poster attached (2010), 1 page.
Minassian, K. et al., "Neuromodulation of lower limb motor control in restorative neurology", Clinical Neurology and Neurosurgery, vol. 114, (2012), pp. 489-497.
Minassian et al., "Mechanisms of rhythm generation of the human lumbar spinal cord in repose to tonic stimulation without and with step-related sensory feedback", Biomed Tech, vol. 58, (Suppl. 1), (2013), 3 pages.
Minev, I. R. et al., "Electronic dura mater for long-term multimodal neural interfaces," Science Magazine, vol. 347, No. 6218, (Jan. 9, 2015), 64 pages.
Minoux, M., Accelerated greedy algorithms for maximizing submodular set functions. Optimization Techniques, LNCS, (1978), pp. 234-243.
Moraud, E. et al., "Mechanisms Underlying the Neuromodulation of Spinal Circuits for Correcting Gait and Balance Deficits after Spinal Cord Injury," Neuron, vol. 89, No. 4, Published Online Feb. 4, 2016, (Feb. 17, 2016), 15 pages.
Murg, M et al., "Epidural electric stimulation of posterior structures of the human lumbar spinal cord: 1. Muscle twitches—a functional method to define the site of stimulation", Spinal Cord, vol. 38, (2000), pp. 394-402.
Musienko, P. et al. "Multi-system neurorehabilitative strategies to restore motor functions following severe spinal cord injury," Experimental Neurology, vol. 235, No. 1, Published Online Sep. 7, 2011, (May 2012), 10 pages.
Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Published Online Jul. 24, 2009, (Nov. 2009), 5 pages.
Musienko, P. et al., "Controlling specific locomotor behaviors through multidimensional monoaminergic modulation of spinal circuitries," The Journal of Neuroscience, vol. 31, No. 25, (Jun. 22, 2011), 32 pages.
Musselman, K. et al., "Spinal Cord Injury Functional Ambulation Profile: A New Measure of Walking Ability," Neurorehabilitation and Neural Repair, vol. 25, No. 3, Published Online Feb. 25, 2011, (Mar. 2011), 9 pages.

Nandra, M. S. et al., "A parylene-based microelectrode array implant for spinal cord stimulation in rats", Conference Proceedings IEEE Eng. Med. Biol. Soc., (2011), pp. 1007-1010.
Nandra, M. S. et al., "A wireless microelectrode implant for spinal cord stimulation and recording in rats", Presentation Abstract, 2013.
Nessler, J. et al., "A Robotic Device for Studying Rodent Locomotion After Spinal Cord Injury," IEEE Transactions on Neural Systems and Rehabilitation Engineering, vol. 13, No. 4, (Dec. 12, 2005), 10 pages.
Pearson, K. G., "Generating the walking gait: role of sensory feedback," Progress in Brain Research, vol. 143, Chapter 12, Published Online Nov. 28, 2003, (2004), 7 pages.
Phillips, A. et al., "Perturbed and spontaneous regional cerebral blood flow responses to changes in blood pressure secondary high-level spinal cord injury: the effect of midodrine," Journal of Applied Physiology, vol. 116, No. 6, Available Online Jan. 16, 2014, (Mar. 15, 2014), 20 pages.
Phillips, A. et al., "Regional neurovascular coupling and cognitive performance in those with low blood pressure secondary to high-level spinal cord injury: improved by alpha-1 agonist midodrine hydrochloride," Journal of Cerebral Blood Flow & Metabolism, vol. 34, No. 5, (May 2014), 8 pages.
Phillips, A. A. et al., "Contemporary Cardiovascular Concerns after Spinal Cord Injury: Mechanisms, Maladaptations, and Management," Journal of Neurotrama, vol. 32, No. 24, (Dec. 15, 2015), 17 pages.
Pratt, G. et al., "Stiffness Isn't Everything," Proceedings of the Fourth International Symposium on Experimental Robotics, (Jun. 30, 1995), 6 pages.
Pratt, J. et al., "Series elastic actuators for high fidelity force control," Industrial Robot: An International Journal, vol. 29, No. 3, Available as Early as Jan. 1, 2002, (1995), 13 pages.
Prochazka, A. et al., "Ensemble firing of muscle afferents recorded during normal locomotion in cats," The Journal of Physiology, vol. 507, No. 1, (Feb. 15, 1998), 12 pages.
Prochazka, A. et al., "Models of ensemble filing of muscle spindle afferents recorded during normal locomotion in cats," The Journal of Physiology, vol. 507, No. 1, (Feb. 15, 1998), 15 pages.
Pudo, D. et al., "Estimating Intensity Fluctuations in High Repetition Rate Pulse Trains Generated Using the Temporal Talbot Effect", IEEE Photonics Technology Letters, vol. 18, No. 5, (Mar. 1, 2006), 3 pages.
Rasmussen, C. E. et al., "Gaussian Processes for Machine Learning", The MIT Press, Cambridge, Massachusetts, (2006), 266 pages.
Rasmussen, C. E. et al., "Gaussian Processes for Machine Learning (GPML) Toolbox", The Journal of Machine Learning Research, vol. 11, (2010), pp. 3011-3015.
Rasmussen, C. E. "Gaussian Processes in Machine Learning", L.N.A.I., vol. 3176, (2003) pp. 63-71.
Rattay, F. et al., "Epidural electrical stimulation of posterior structures of the human lumbosacral cord: 2. Quantitative analysis by computer modeling", Spinal Cord, vol. 38, (2000), pp. 473-489.
Reinkensmeyer, D. et al., "Tools for understanding and optimizing robotic gait training," Journal of Rehabilitation Research & Development, vol. 43, No. 5, (Aug. 2006), 14 pages.
Rejc, E. et al., "Effects of Lumbosacral Spinal Cord Epidural Stimulation for Standing after Chronic Complete Paralysis in Humans," PLoS One, vol. 10, No. 7, (Jul. 24, 2015), 20 pages.
Robbins, H., "Some Aspects of the Sequential Design of Experiments", Bull. Amer. Math. Soc., vol. 58, (1952), pp. 527-535.
Rodger, D. C. et al., "High Density Flexible Parylene-Based Multielectrode Arrays for Retinal and Spinal Cord Stimulation", Proc. of the 14th International Conference on Solid-State Sensors, Actuators and Microsystems, (2007), pp. 1385-1888.
Rosenzweig, E. et al., "Extensive Spontaneous Plasticity of Corticospinal Projections After Primate Spinal Cord Injury", Nature Neuroscience, vol. 13, No. 12, Published Online Nov. 14, 2010, (Dec. 2010), 19 pages.
Ryzhov, I. O. et al., "The knowledge gradient algorithm for a general class of online learning problems", Operations Research, vol. 60, No. 1, (2012), pp. 180-195.

(56) References Cited

OTHER PUBLICATIONS

Sayenko, D. et al., "Neuromodulation of evoked muscle potentials induced by epidural spinal-cord stimulation in paralyzed individuals," Journal of Neurophysiology, vol. 111, No. 5, Published Online Dec. 11, 2013, (2014), 12 pages.
Shamir, R. R. et al., "Machine Learning Approach to Optimizing Combined Stimulation and Medication Therapies for Parkinson's Disease," Brain Stimulation, vol. 8, No. 6, Published Online Jun. 15, 2015, (Nov. 2015), 22 pages.
Srinivas, N. et al., "Gaussian process optimization in the bandit setting: No regret and experimental design", In Proceedings of the 27th International Conference on Machine Learning, (2010), 17 pages.
Steward, O. et al., "False Resurrections: Distinguishing Regenerated from Spared Axons in the Injured Central Nervous System", The Journal of Comparative Neurology, vol. 459, No. 1, (Apr. 21, 2003), 8 pages.
Stienen, A. H. A. et al., "Analysis of reflex modulation with a biologically realistic neural network," Journal of Computer Neuroscience, vol. 23, No. 3, Available Online May 15, 2007, (Dec. 2007),16 pages.
Sun, F. et al., "Sustained axon regeneration induced by co-deletion of PTEN and SOCS3", Nature, vol. 480, No. 7377, Published Online Nov. 6, 2011, (Dec. 15, 2011),12 pages.
Takeoka, A. et al., "Muscle Spindle Feedback Directs Locomotor Recovery and Circuit Reorganization after Spinal Cord Injury", Cell, vol. 159, No. 7, (Dec. 18, 2014), 27 pages.
Tenne, Y. et al., "Computational Intelligence in Expensive Optimization Problems", vol. 2 of Adaptation, Learning, and Optimization, Springer, Berlin Heidelberg, (2010), pp. 131-162.
Timozyk, W. et al., "Hindlimb loading determines stepping quantity and quality following spinal cord transection," Brain Research, vol. 1050, No. 1-2, Published Online Jun. 24, 2005, (Jul. 19, 2005), 10 pages.
Vallery, H. et al., "Compliant Actuation of Rehabilitation Robots," IEEE Robotics & Automation Magazine, vol. 15, No. 3, (Sep. 12, 2008), 10 pages.
Van Den Brand, R. et al., "Restoring Voluntary Control of Locomotion after Paralyzing Spinal Cord Injury," Science Magazine, vol. 336, No. 6085, (Jun. 1, 2012), 5 pages.
Wan, D. et al., "Life-threatening outcomes associated with autonomic dysreflexia: A clinical review," Journal of Spinal Cord Medicine, vol. 37, No. 1, (Jan. 2014), 9 pages.
Ward, A. R., "Electrical Stimulation Using Kilohertz-Frequency Alternating Current", Physical Therapy, vol. 89, Published online Dec. 18, 2008, (2009), pp. 181-190.
Wenger, N. et al., "Supplementary Materials for Closed-loop neuromodulation of spinal sensorimotor circuits controls refined locomotion after complete spinal cord injury," Science Translational Medicine, vol. 6, No. 255, Sep. 24, 2014, 14 pages.
Wenger, N. et al., "Spatiotemporal neuromodulation therapies engaging muscle synergies improve motor control after spinal cord injury," Natural Medicine, vol. 22, No. 2, Available Online Jan. 18, 2016, (Feb. 2016), 33 pages.
Wenger, N. et al. "Closed-loop neuromodulation of spinal sensorimotor circuits controls refined locomotion after complete spinal cord injury" Sci Transl. Med., vol. 6, Issue 255, Sep. 24, 2014), 10 pages.
Wernig, A. et al., "Laufband locomotion with body weight support improved walking in persons with severe spinal cord injuries", Paraplegia, vol. 30, No. 4, (Apr. 1992), 10 pages.
Wernig, A., "Ineffectiveness of Automated Locomotor Training," Archives of Physical Medicine and Rehabilitation, vol. 86, No. 12, (Dec. 2005), 2 pages.
Wessels, M. et al., "Body Weight-Supported Gait Training for Restoration of Walking in People With an Incomplete Spinal Cord Injury: A Systematic Review," Journal of Rehabilitation Medicine, vol. 42, No. 6, (Jun. 2010), 7 pages.
Widmer, C. et al., Inferring latent task structure for multitask learning by multiple kernel learning, BMC Bioinformatics, vol. 11, (Suppl 8:S5), (2010), 8 pages.
Winter, D. A. et al., "An integrated EMG/biomechanical model of upper body balance and posture during human gait," Progress in Brain Research, vol. 97, Ch. 32, Available as Early as Jan. 1, 1993, (1993), 9 pages.
Wirz, M. et al., "Effectiveness of automated locomotor training in patients with acute incomplete spinal cord injury: A randomized controlled multicenter trial," BMC Neurology, vol. 11, No. 60, (May 27, 2011), 9 pages.
Yakovenko, S. et al., "Spatiotemporal Activation of Lumbosacral Motoneurons in the Locomotor Step Cycle," Journal of Neurophysiology, vol. 87, No. 3, (Mar. 2002), 12 pages.
Zhang, T. C. et al., "Mechanisms and models of spinal cord stimulation for the treatment of neuropathic pain," Brain Research, vol. 1569, Published Online May 4, 2014, (Jun. 20, 2014), 13 pages.
Zorner, B. et al., "Profiling locomotor recovery: comprehensive quantification of impairments after CNS damage in rodents," Nature Methods, vol. 7, No. 9, Published Online Aug. 15, 2010, (Sep. 2010), 11 pages.

* cited by examiner

SYSTEM FOR NEUROMODULATION

CROSS-REFERENCE TO RELATED APPLICATION

The present application claims priority to European Patent Application No 19156617.3, filed on Feb. 12, 2019. The entire contents of the above-listed application is hereby incorporated by reference for all purposes.

TECHNICAL FIELD

The present invention relates to systems and methods for neuromodulation, especially neurostimulation.

BACKGROUND AND SUMMARY

Decades of research in physiology have demonstrated that the mammalian spinal cord embeds sensorimotor circuits that produce movement primitives (cf. Bizzi E, et al., *Modular organization of motor behavior in the frog's spinal cord. Trends in neurosciences* 18, 442-446 (1995); Levine A J, et al., *Identification of a cellular node for motor control pathways. Nature neuroscience* 17, 586-593 (2014)). These circuits process sensory information arising from the moving limbs and descending inputs originating from various brain regions in order to produce adaptive motor behaviors.

A spinal cord injury (SCI) interrupts the communication between the spinal cord and supraspinal centers, depriving these sensorimotor circuits from the excitatory and modulatory drives necessary to produce movement.

In general, neural stimulation may be achieved by electrical stimulation, optogenetics (optical neural stimulation), chemical stimulation (implantable drug pump), ultrasound stimulation, magnetic field stimulation, mechanical stimulation, etc.

A series of studies in animal models and humans showed that electrical neuromodulation of the lumbar spinal cord using Epidural Electrical Stimulation (EES) is capable of (re-)activating these circuits. For example, EES has restored coordinated locomotion in animal models of SCI, and isolated leg movements in individuals with motor paralysis (cf van den Brand R, et al., *Restoring Voluntary Control of Locomotion after Paralyzing Spinal Cord Injury. Science* 336, 1182-1185 (2012); Angeli C A, et al., *Altering spinal cord excitability enables voluntary movements after chronic complete paralysis in humans. Brain: a journal of neurology* 137, 1394-1409 (2014); Harkema S, et al., *Effect of epidural stimulation of the lumbosacral spinal cord on voluntary movement, standing, and assisted stepping after motor complete paraplegia: a case study. The Lancet* 377, 1938-1947 (2011); Danner S M, et al., *Human spinal locomotor control is based on flexibly organized burst generators. Brain: a journal of neurology* 138, 577-588 (2015); Courtine G, et al., *Transformation of nonfunctional spinal circuits into functional states after the loss of brain input. Nature neuroscience* 12, 1333-1342, (2009); Capogrosso M, et al., *A brain-spine interface alleviating gait deficits after spinal cord injury in primates. Nature* 539, 284-288, (2016)).

Computational models (cf Capogrosso M, et al., *A computational model for epidural electrical stimulation of spinal sensorimotor circuits. The Journal of neuroscience: the official journal of the Society for Neuroscience* 33, 19326-19340 (2013); Moraud E M et al., *Mechanisms Underlying the Neuromodulation of Spinal Circuits for Correcting Gait and Balance Deficits after Spinal Cord Injury. Neuron* 89, 814-828 (2016); Rattay F, et al., *Epidural electrical stimulation of posterior structures of the human lumbosacral cord: 2. quantitative analysis by computer modeling. Spinal cord* 38, 473-489 (2000)) and experimental studies (cf. Gerasimenko Y, et al., Program No. 447.445 (*Soc. Neurosci. Abstr*); Minassian K, et al., *Human lumbar cord circuitries can be activated by extrinsic tonic input to generate locomotor-like activity. Human Movement Science* 26, 275-295 (2007)) have provided evidence suggesting that EES recruits large-diameter sensory afferents, especially proprioceptive circuits (cf. Moraud E M, et al., *Mechanisms Underlying the Neuromodulation of Spinal Circuits for Correcting Gait and Balance Deficits after Spinal Cord Injury. Neuron* 89, 814-828, (2016)).

Consequently, the stimulation leads to the activation of motoneurons through mono- and polysynaptic proprioceptive circuits, as well as increases the general excitability of the lumbar spinal cord. In addition, the natural modulation of proprioceptive circuits during movement execution gates the effects of EES towards functionally relevant spinal pathways. Concretely, due to phase-dependent modulation of proprioceptive circuits, the effects of stimulation are restricted to specific ensembles of leg motoneurons that are coherent with the phase of the movement (cf. Moraud E M, et al., *Mechanisms Underlying the Neuromodulation of Spinal Circuits for Correcting Gait and Balance Deficits after Spinal Cord Injury. Neuron* 89, 814-828 (2016)).

Moreover, since EES engages motoneurons through trans-synaptic mechanisms, residual inputs from supraspinal centres are also capable of gating the effects of EES towards specific circuits or increasing the excitability of the motoneuron pools (and thus their responsiveness to EES) in order to mediate voluntary modulation of leg movements (cf van den Brand R, et al., *Restoring Voluntary Control of Locomotion after Paralyzing Spinal Cord Injury. Science* 336, 1182-1185 (2012); Angeli C A, et al., Altering spinal cord excitability enables voluntary movements after chronic complete paralysis in humans. Brain: a journal of neurology 137, 1394-1409 (2014); Harkema, S, et al. Effect of epidural stimulation of the lumbosacral spinal cord on voluntary movement, standing, and assisted stepping after motor complete paraplegia: a case study. The Lancet 377, 1938-1947).

This conceptual framework was exploited to design a neuromodulation strategy that targets specific ensembles of proprioceptive afferents associated with flexion and extension of both legs (cf. Bizzi E, et al., *Modular organization of motor behavior in the frog's spinal cord. Trends in neurosciences* 18, 442-446 (1995); Levine A J, et al. *Identification of a cellular node for motor control pathways. Nature neuroscience* 17, 586-593 (2014)).

This strategy, termed spatiotemporal neuromodulation, consists of delivering EES bursts through targeted electrode configurations with a temporal structure that reproduces the natural activation of leg motoneurons during locomotion. This spatiotemporal neuromodulation therapy reversed leg paralysis in both rodent and primate models of SCI (cf. Capogrosso M, et al., *A brain-spine interface alleviating gait deficits after spinal cord injury in primates. Nature* 539, 284-288, (2016); Wenger N et al., *Spatiotemporal neuromodulation therapies engaging muscle synergies improve motor control after spinal cord injury. Nat Med* 22, 138-145 (2016)).

This conceptual framework is applicable to develop spatiotemporal neuromodulation therapies for enabling leg motor control in humans with SCI.

Generally speaking, known stimulation systems use either Central Nervous System (CNS) stimulation, especially Epidural Electrical Stimulation (EES), or Peripheral Nervous System (PNS) stimulation, especially Functional Electrical Stimulation (FES).

EES is known to restore motor control in animal and human models and has more particularly been shown to restore locomotion after spinal cord injury by artificially activating the neural networks responsible for locomotion below the spinal cord lesion (cf. Capogrosso M, et al., *A Computational Model for Epidural Electrical Stimulation of Spinal Sensorimotor Circuits, Journal of Neuroscience* 4 Dec. 2013, 33 (49) 19326-19340; Courtine G, et al., *Transformation of nonfunctional spinal circuits into functional states after the loss of brain input*, Nat Neurosci. 2009 October; 12(10): 1333-1342; Moraud E M, et al, *Mechanisms Underlying the Neuromodulation of Spinal Circuits for Correcting Gait and Balance Deficits after Spinal Cord Injury, Neuron* Volume 89, Issue 4, p 814-828, 17 Feb. 2016). EES does not directly stimulate motor-neurons but the afferent sensory neurons prior to entering into the spinal cord. In this way, the spinal networks responsible for locomotion are recruited indirectly via those afferents, restoring globally the locomotion movement by activating the required muscle synergies. The produced movement is functional; however, due to relatively poor selectivity (network activation instead of selective targeting of key muscles) the controllability is low and the imprecisions hinder fluidity and full functionality in the potential space of the movement.

PNS stimulation systems used to date in the clinic are known as FES that provides electrical stimulation to target muscles with surface electrodes, either directly through stimulation of their motorfibers (neuro-muscular stimulation), or through a limited set reflexes (practically limited to the withdrawal reflex) or by transcutaneously stimulating the peripheral nerves. The resulting muscle fatigue has rendered FES unsuitable for use in daily life. Furthermore, successes have remained limited through cumbersome setups when using surface muscle stimulation, unmet needs in terms of selectivity (when using transcutaneous nerve stimulation) and a lack of stability (impossible to reproduce exact electrode placement on a daily basis when stimulating muscles, moving electrodes due to clothes, sweating).

EP 2 868 343 A1 discloses a system to deliver adaptive electrical spinal cord stimulation to facilitate and restore locomotion after neuromotor impairment. Inter alia, a closed-loop system for real-time control of EES is disclosed, the system comprising means for applying to a subject neuromodulation with adjustable stimulation parameters, said means being operatively connected with a real-time monitoring component comprising sensors continuously acquiring feedback signals from said subject. The feedback signals provide features of motion of a subject, wherein the real-time monitoring component is operatively connected with a signal processing device receiving feedback signals and operating real-time automatic control algorithms. This known system improves consistency of walking in a subject with a neuromotor impairment. Reference is also made to Wenger N et al., *Closed-loop neuromodulation of spinal sensorimotor circuits controls refined locomotion after complete spinal cord injury, Science Translational Medicine*, 6, 255 (2014).

WO 2002/034331 A2 discloses a non-closed loop implantable medical device system that includes an implantable medical device, along with a transceiver device that exchanges data with the patient, between the patient and the implantable medical device, and between a remote location and the implantable medical device. A communication device coupled to the transceiver device exchanges data with the transceiver device, the implantable medical device through the receiver device, and between the transceiver device and the remote location to enable bi-directional data transfer between the patient, the implantable medical device, the transceiver device, and the remote location. A converter unit converts transmission of the data from a first telemetry format to a second telemetry format, and a user interface enables information to be exchanged between the transceiver device and the patient, between the implantable medical device and the patient through the transceiver device, and between the patient and the remote location through the transceiver device.

EP 3 184 145 discloses systems for selective spatiotemporal electrical neurostimulation of the spinal cord. A signal processing device receiving signals from a subject and operating signal-processing algorithms to elaborate stimulation parameter settings is operatively connected with an implantable pulse generator (IPG) receiving stimulation parameter settings from said signal processing device and able to simultaneously deliver independent current or voltage pulses to one or more multiple electrode arrays. The electrode arrays are operatively connected with one or more multi-electrode arrays suitable to cover at least a portion of the spinal cord of said subject for applying a selective spatiotemporal stimulation of the spinal circuits and/or dorsal roots, wherein the IPG is operatively connected with one or more multi-electrode arrays to provide a multipolar stimulation. Such system advantageously allows achieving effective control of locomotor functions in a subject in need thereof by stimulating the spinal cord, in particular the dorsal roots, with spatiotemporal selectivity.

WO 2017/062508 A1 discloses a system for controlling a therapeutic device and/or environmental parameters including one or more body worn sensor devices that detect and report one or more physical, physiological, or biological parameters of a person in an environment. The sensor devices can communicate sensor data indicative of the one or more physical, physiological, or biological parameters of a person to an external hub that processes the data and communicates with the therapeutic device to provide a therapy (e.g., neuromodulation, neurostimulation, or drug delivery) as a function of the sensor data. In some embodiments, the therapeutic device can be implanted in the person. In some embodiments, the therapeutic device can be in contact with the skin of the person. The sensor devices can also communicate to the hub that communicates with one or more devices to change the environment as a function of the sensor data.

WO2016/110804 A1 describes a number of inventions comprising one or more wearable devices (i.e. attached or applied to limbs, body, head or other body extremities but also applicable to implanted or physiologically attachable systems). These systems have a means of enabling diagnostic or prognostic monitoring applicable to monitoring relevant parameters and corresponding analysis determination and characterization applicable to the onset or detection of events or health conditions of interest.

WO2017/058913 relates to systems and methods to analyze gait, balance or posture information extracted from data collected by one or more wearable and connected sensor devices with sensors embedded there within. Sensor data detected by the sensors can be received by a mobile computing device, which can analyze the sensor data to identify a pattern related to gait, balance or posture within the sensor data; and apply a statistical/machine learning-based classification to the pattern related to gait, balance or posture to assign a clinical parameter to the pattern characterizing a risk of a slip, trip and fall event.

WO2005/002663 A2 discloses a method for generating an electrical signal for use in biomedical applications, including two timing-interval generators, each optionally driving a multistep sequencer; analog, digital or hybrid means for combining the resulting timed signals into a complex electrical signal; optional filtering means for blocking direct current, removing selected frequency components from the resulting signal, and/or providing voltage stepup if needed; and conductive means for coupling the resulting signal to a human or animal body, food, beverage or other liquid, cell or tissue culture, or pharmaceutical material, in order to relieve pain, stimulate healing or growth, enhance the production of specific biochemicals, or devitalize selected types of organisms.

According to the state of the art, smooth movements comparable to healthy subjects still cannot be achieved by neuromodulation of the subject. There is no available system which overcomes the drawbacks of the prior art. In particular, there is the need of a system stimulating the patient not as a robot. A good roll of the foot and no parasite movements are necessary during walking and smooth movements are necessary during any other movement including but not limited to one or more of cycling, swimming, rowing, stepping, sitting down, and standing up. Thus, the goal of applying stimulation is not to control the patient as a robot, but to support the patient during training and daily life activities, including but not limited to one or more of walking, cycling, swimming, rowing, stepping, sitting down, standing up, and any other movement.

Thus, a control system should enable real-time synchronization of stimulation and motion.

It is an objective of the present invention to improve a neuromodulation system, preferably a neurostimulation system, e.g. in the field of improving recovery after neurological disorders like spinal cord injury (SCI), for example after trauma, especially in synchronizing stimulation and a feedback acquisition system.

This objective is solved according to the present invention by a neuromodulation system movement reconstruction and/or restoration of a patient, with the features of claim 1. Accordingly, a neuromodulation system comprising:

at least one stimulation element,
at least one stimulation controller and
at least one stimulation feedback acquisition system, further comprising
a reference trigger input module configured such that temporal relationship between a provided stimulation via the stimulation element and the stimulation controller and a stimulation response received by the stimulation feedback acquisition system can be characterized.

The invention is based on the basic idea that in the context of neuromodulation, especially neurostimulation, the electrical stimulation parameters defining the stimulation for a patient can be controlled with said system, wherein a reference trigger signal is provided, such that the temporal and/or spatial and/or spatio-temporal relationship between stimulation and the actual received response of the stimulation can be characterized. The temporal relationship may be used to improve stimulation sequences for a desired type of movement.

The actual received response may include any physiological response to the stimulation obtained by a feedback acquisition system. The use of a general concept including at least one stimulation element, at least one stimulation controller, at least one stimulation feedback acquisition system, and a reference trigger input module for neuromodulation system for a patient being equipped with the neuromodulation system enables triggering neurostimulation based on a determined temporal relationship between stimulation and acquisition of feedback. In other words, the temporal relationship, or temporal difference, caused by the feedback acquisition system may be corrected based on the reference trigger input module. As a consequence, the system may enable realtime stimulation of a patient during a task and/or movement. In particular, as the temporal relationship between stimulation provided by the stimulation element and the physiological response may have been characterized, the stimulation element may provide stimulation to the patient such that realtime movements are enabled. In other words, the stimulation may be correlated in time with the physiological response.

In doing so, the system my overcome manual tuning and/or timing by a therapist and/or physiotherapist.

The neuromodulation system may interfere with the natural feedback loop of the patient to enable smooth motion, e.g. a regular gait cycle comparable to a healthy subject.

The system can be used for treatment related but not limited to restoring and/or training of the movements of the patient. These movements may include but are not limited to walking, running, stepping, swimming, cycling, rowing, standing up and/or sitting down. However, also other types of cyclic and non-cyclic movements are possible. The system may be also applied for a patient being supported by an external device, including but not limited to body-weight support, a walker, or crutches.

The stimulation controller may be configured and arranged to provide stimulation control signals to the stimulation element. The stimulation controller may process data that is acquired among others from the stimulation element, the stimulation feedback acquisition system and the reference trigger input module. In particular, the stimulation controller may be a body-worn platform to execute the control software.

The stimulation feedback acquisition system may be configured and arranged to assess any type of direct and/or indirect stimulation response, including but not limited to motion, electrical excitation signals and/or heat.

The feedback acquisition system may continuously acquire data.

A trigger signal may be used during data acquisition in order to characterize when a stimulation event has been provided by the stimulation element, such that after providing the stimulation, the physiological response to the stimulation can be captured and distinguished from the background, including but not limited to noise and/or other artefacts.

In general, a trigger signal provided by a neuromodulation system may be essential for performing reliable event-detection by an algorithm responsible for processing acquired physiological signals. Since physiological signals are very prone to various disturbances and artefacts, the likelihood of false positives may increase when the system does not comprise a reference trigger input module processing trigger signals and respective physiological responses.

The stimulation controller, the stimulation element and/or the stimulation feedback acquisition system are not synchronized by nature. In particular, the characterization of the temporal relationship enables synchronizing the clocks of the stimulation element, the stimulation controller, the feedback acquisition system and the reference trigger input module. If further subsystems are included in the neuromodulation system, the temporal relationship between all subsystems may be corrected by synchronization of the clocks of said further subsystems.

The temporal relationship may be a time delay. Thus, the neuromodulation system may characterize, manage, and/or correct for the time delay occurring between stimulation initiated by the stimulation controller and/or stimulation element and/or the stimulation feedback acquisition system and/or the reference trigger input module. As a consequence, said neuromodulation system enables, inter alia, triggering or synchronizing stimulation element and stimulation feedback acquisition system.

The at least one stimulation feedback acquisition system may comprise a stimulation feedback acquisition base station and/or at least one sensor. The sensor may be or may comprise at least one of a sequence of event sensor, motion sensor, EMG, afferent signal sensor, efferent signal sensor, impedance sensor, EEG, BCI and camera-based system. The EMG sensor may be a surface or intramuscular electrode or array of electrodes.

In particular, the at least one sensor could be configured and arranged to be implemented as a camera-based system that detects muscular activation.

In particular, an implanted stimulation element and/or stimulation electrode and/or array of electrodes could also be used as a sensor.

In particular, the at least one sensor may enable detection of any type of stimulation response, including but not limited to motion, electrical excitation signals and/or heat. The at least one sensor may be configured and arranged to be inserted into and/or attached to the patient's body and/or parts of the patient's body, including but not limited to at least one upper and/or lower limb, the head, the trunk, the neck, the hips, and/or the abdomen of a patient. Alternatively, the sensors may be integrated into and/or attached onto a training device or auxiliary therapeutic equipment, including but not limited to an exoskeleton, physiotherapy beds or any type of clothing.

Furthermore, the stimulation feedback acquisition system may comprise at least two identical and/or nonidentical sensors, wherein the at least two sensors are synchronized. Of note, in the case that the stimulation feedback acquisition system may comprise more than two sensors it may be possible that only some sensors are synchronized. Alternatively, all sensors of the stimulation feedback acquisition system may be synchronized.

In particular, the two or more sensors may form a sensor network. The sensor network may be a wireless sensor network.

Further, the neuromodulation system may comprise one or more subsystems, wherein the subsystems comprise at least one of a programmer, a passive electrical component, a microprocessor, a wireless link (WL), a communication module (COM) and/or a telemetry module (TEL) module.

The programmer may be used to receive inter alia stimulation parameters, patient data, physiological data, training data etc. The programmer may be an application installed on a mobile device that communicates with the stimulation controller. The programmer may be used by a therapist, physiotherapist, or patient to provide inputs to the stimulation controller, e.g., selecting, starting, and stopping a task or configuring stimulation parameters.

The programmer should allow adjusting the stimulation parameters of a task, while the task is running. This enables the user to tune the stimulation without having to start and stop the task, which would be very cumbersome at the start of the rehabilitation training, when all the stimulation parameters are developed and tuned.

The programmer may include but is not limited to a physiotherapist programmer (PTP), and patient programmer (PP) which are applications installed on a mobile device that communicate with the controller. These programmers may aim at providing functionalities for different levels of professional expertise in the field of rehabilitation and as such could, respectively, provide advanced stimulation options with trigger-capabilities to physiotherapists and simpler forms of trigger-capabilities to patients.

This wireless network may link the stimulation controller and the stimulation element and/or the feedback acquisition system and/or the reference trigger input module and/or any other subsystem including but not limited to a programmer and/or a microprocessor of the neuromodulation system to send data and receive data. This also may include error-correction, retries, commands including but not limited to start or stopping a task.

The communication module may be or may comprise a Bluetooth module and the telemetry module may be or may comprise a Near Field Magnetic Induction (NFMI) module or a Near Field Electromagnetic Induction module (NFEMI). Alternatively, and/or additionally, the telemetry module may be or may comprise one or more of a Medical Implant Communication System (MICS) and/or one or more of a Medical Data Service System (MEDS).

MICS is a low-power, short-range, high-data-rate 401-406 MHz (the core band is 402-405 MHz) communication network.

Similarly, MEDS systems may operate in spectrum within the frequency bands 401 MHz to 402 MHz and 405 MHz to 406 MHz.

In particular, the communication module may be a wireless link between the stimulation controller and the stimulation element and/or the stimulation feedback acquisition system and/or the reference trigger input module and/or any other subsystem including but not limited to a programmer and/or a microprocessor and/or a connector of the neuromodulation system to send data and receive data. This also may include error-correction, retries, commands including but not limited to start or stopping a task.

Furthermore, the stimulation controller may be configured and arranged to provide a reference trigger signal, wherein the reference trigger signal is recorded by the stimulation feedback acquisition system.

In particular, the reference trigger signal may be at least one of a electrical signal, a Bluetooth signal, an NFMI signal and an NFEMI signal. This reference trigger signal may enable synchronization of the stimulation element and the stimulation feedback acquisition system. In general, it could be possible that the reference trigger signal is used to start data acquisition of the stimulation feedback acquisition system, in particular to start data acquisition of the sensor of the stimulation feedback acquisition system. Similarly, in addition to or rather than starting/stopping acquisition, the reference trigger may be used as time-marker in a signal acquired over a timeperiod to segment specific temporal segments of that data for further processing.

Of note, the reference trigger signal may also allow synchronization of other systems and/or elements and/or subsystems being part of the neuromodulation system. The above-mentioned subsystems may lead to various delays in said neuromodulation system. However, the reference trigger input system module may be configured and arranged such that the temporal relationship, e.g. time delay, between the various subsystems can be characterized and/or managed and/or corrected.

Furthermore, the stimulation controller may be configured and arranged to be connected to a connector, wherein the connector is connected to the stimulation feedback acquisition system. In particular, the connector may be connected to the feedback acquisition base station and/or at least one sensor of the stimulation feedback acquisition system.

Furthermore, a passive electrical component may be configured and arranged to convert a NFMI signal into an electrical signal, wherein the response and/or the transmission of the electrical signal is recorded by the stimulation feedback acquisition system. In particular, a NFMI signal provided by the stimulation controller may be converted by the passive electrical component into an electric signal, wherein the response and/or the transmission of the electrical signal may be recorded by the stimulation feedback acquisition system. Of note, any other type of signal provided by the simulation controller including but not limited to a NFMI signal, a NFEMI signal, and/or a Bluetooth signal could be converted by a passive electrical component into any other type of signal, including but not limited to an electric signal.

In particular, the passive electrical component may be configured and arranged to be included in a sticker, wherein the sticker may be attached to the skin of a patient. In particular, the passive electrical component may be included in and/or attached onto the sticker. Of note, the sticker may be placed on any part of the body of the patient. In particular, the passive electrical component may pick up the magnetic field, i.e. the NFMI signal, provided by the stimulation controller and convert it into an electric field onto the sticker attached to the skin of the patient. In particular, the electrical field may propagate from the sticker attached to the skin of the patient over the skin of the patient, thereby changing skin potential. In particular, this change in skin potential may be recorded by the stimulation feedback acquisition system. Thereby, the signal could serve as a reference trigger signal for the stimulation feedback acquisition system.

Alternatively, the passive electrical component may be configured and arranged to be inserted and/or integrated into and/or onto the clothing of the patient, including but not limited to a top, a longsleeve, a pullover, a jacket, one or more gloves, armlets, socks, tights, a belt and/or a pouch worn by the patient equipped with the system. The passive electrical component may be in direct contact with the skin of the patient. Furthermore, the stimulation element may be configured and arranged to provide an under-threshold signal, wherein the under-threshold signal does not lead to stimulation of a subject but is detectable by the stimulation feedback acquisition system as a reference trigger signal. In particular, the stimulation element and/or the casing of the stimulation element may provide a signal, which does not induce a movement and/or excitation of the patient but may be recorded by the stimulation feedback acquisition system.

In general, it is possible to provide neuromodulation and/or neurostimulation with the stimulation element to the CNS with a CNS stimulation element and/or to the PNS with a PNS stimulation element. Note that the CNS stimulation element and the PNS stimulation element can be comprised in one stimulation element. Both CNS and PNS can be stimulated at the same time or also intermittently or on demand. These two complementary stimulation paradigms can be combined into one strategy and made available for a patient being equipped with the system. For example, neuromodulation and/or neurostimulation of the CNS may be used to enhance and/or restore the patient's capabilities of movement, especially in a way that the existing ways of physiological signal transfer in the patient's body are supported such that the command signals for body movement or the like still are provided by the patient's nervous system and just supported and/or enhanced or translated by the CNS stimulation system. The stimulation provided by a PNS stimulation element may be used to specifically steer and direct stimulation signals to specific peripheral nervous structures in order to trigger a specific movement and/or refine existing movements. Such a PNS stimulation may be used to refine and/or complete motion and/or movement capabilities of the patient being equipped with the system. For example, the PNS stimulation can be used to complete flexion or extension, lifting, turning or the like of inter alia but not limited to toes, fingers, arms, feet, legs or any extremities of the patient. This can be done in cases where it is realized that the neuromodulation and/or neurostimulation provided by the CNS stimulation element is not sufficient to complete a movement of the patient. Then, such a movement may be completed or supported by stimulation provided by the PNS stimulation element. The PNS stimulation can be also used to reduce side effects or compensate for imprecisions of the CNS stimulation.

EES can be phasic or tonic, selective PNS stimulation is always phasic. Here, phasic is defined as locked to defined events in the sensing signals (decoded intention, continuous decoding, muscle activity onset, movement onset, event during defined movement (foot off or foot strike during walking for instance).

By PNS stimulation, a stimulation of the upper limb nerves, i.e. the radial, ulnar and/or median nerves can be provided. All PNS stimulation can be done by targeting nerves with intra-neural electrodes (transversal or longitudinal) or epi-neural (cuff) electrodes.

By CNS stimulation the following nervous structures may be stimulated: for the upper limb movements, the cervical spinal cord or hand/arm motor cortex may be stimulated with the CNS stimulation system. For the lower limb movements, the lumbosacral spinal cord may be stimulated. All these nerves can be targeted with epidural, subdural or intra-spinal/intra-cortical stimulation.

Both PNS and CNS stimulation systems may comprise implantable pulse generators (IPGs).

IPGs can be used for providing the necessary stimulation current and signals for the CNS stimulation element and the PNS stimulation element. The IPG produces the stimulation pulses that are delivered by a lead comprising multiple electrodes to the stimulation site, e.g. the spinal cord.

For EES, the lead is positioned in the epidural space (that is, on the outside of the dural sac, which encases the spinal cord and the cerebrospinal fluid in which the spinal cord 'floats'), on top of the spinal cord (including but not limited to the segments T12, L1, L2, L3, L4, L5, and S1 bilaterally).

It is also possible that two separated IPGs are provided, one for the PNS stimulation element and one for the CNS stimulation element.

The stimulation parameters for the PNS stimulation and the EES stimulation may be frequency, amplitude, pulse-width and the like.

Both CNS and PNS stimulations, as well as the combination of these stimulation systems may be used in a sub-motor threshold region, i.e. an amplitude or configuration at which neuronal sensation but no motor response is evoked.

The control system may be a closed-loop system.

The control system may alternatively be an open-loop system.

BRIEF DESCRIPTION OF THE FIGURES

Further details and advantages of the present invention shall now be disclosed in connection with the drawings.

It is shown in

DETAILED DESCRIPTION

Figure 1:
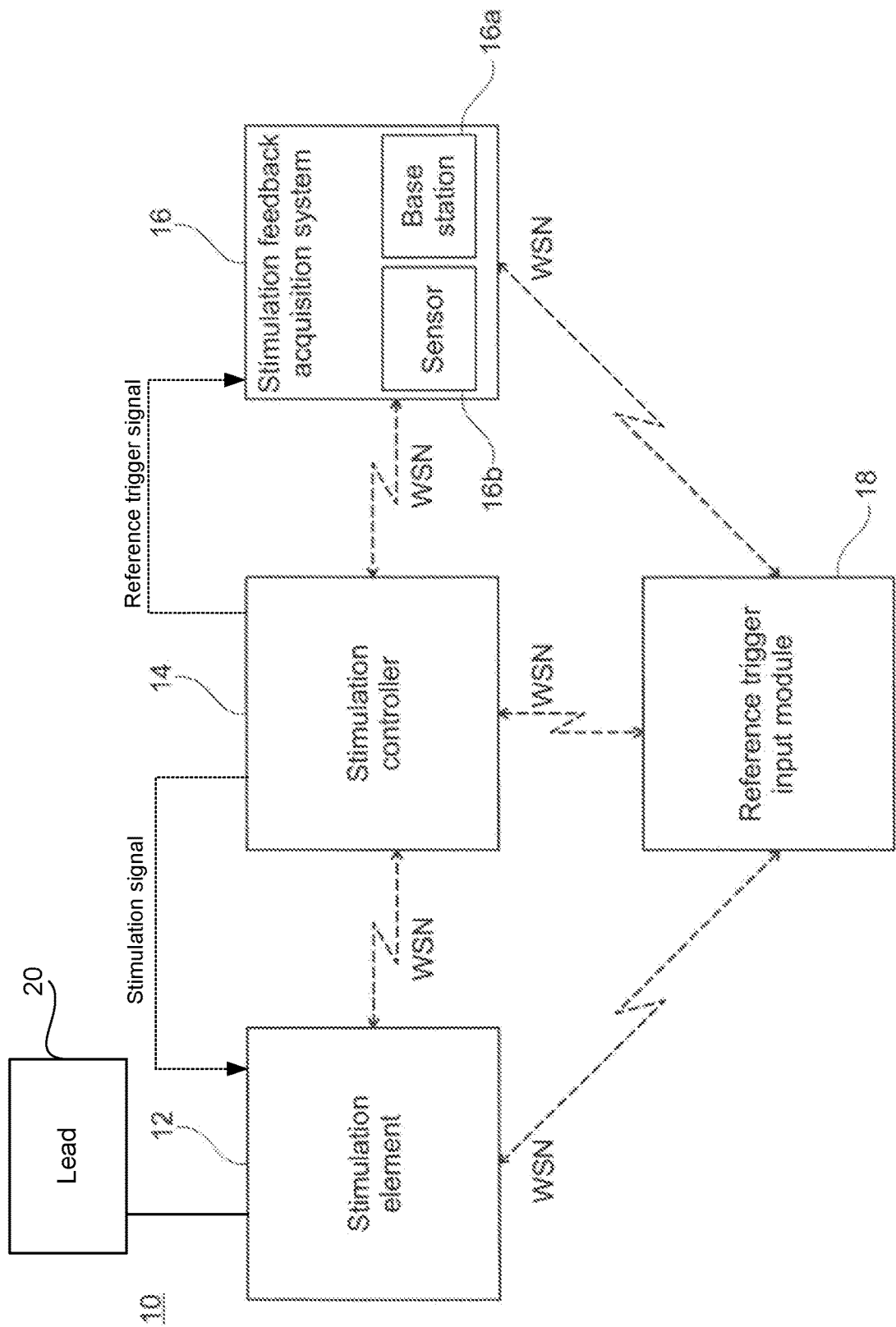
FIG. 1 a general layout of an embodiment of the neuromodulation system for movement reconstruction and/or restoration of a patient according to the present invention.

FIG. 1 shows a general layout of an embodiment of the neuromodulation system 10 for movement reconstruction and/or restoration of a patient according to the present invention.

The neuromodulation system 10 comprises a stimulation element 12.

In this embodiment, the stimulation element 12 is an implantable pulse generator IPG.

In general, any other type of implantable and/or non-implantable stimulation element 12 could be generally possible.

The IPG is implanted in the body of the patient.

The neuromodulation system 10 further comprises a stimulation controller 14.

Additionally, the neuromodulation system comprises a stimulation feedback acquisition system 16.

In this embodiment, the stimulation feedback acquisition system 16 comprises a stimulation feedback acquisition base station 16*a* and a sensor 16*b*.

It could be generally possible that the feedback acquisition system 16 comprises more than one sensor 16*b*.

It could be generally possible that the feedback acquisition system 16 comprises at least two identical and/or non-identical sensors 16*b*.

It could be generally possible that the at least two sensors 16*b* are synchronized.

It could be generally possible that the at least two identical and/or non-identical sensors 16*b* form a sensor network.

There is also a reference trigger input module 18.

The stimulation element 12 is communicatively connected to the stimulation controller 14.

The stimulation element 12 is also communicatively connected to the reference trigger input module 18.

The connection between the stimulation element 12 and the stimulation controller 14 and the stimulation element 12 and the reference trigger input module 18 is in the shown embodiment a direct and bidirectional connection.

However, also an indirect and/or unidirectional connection (i.e. with another component of the neuromodulation 10 in between) would be generally possible.

The connection between the stimulation element 12 and the stimulation controller 14 and the stimulation element 12 and the reference trigger input module 18 is established in the shown embodiment by a wireless network WSN.

However, also a cable bound connection would be generally possible.

Moreover, the stimulation controller 14 is connected to the stimulation feedback acquisition system 16.

The stimulation controller 14 is also connected to the reference trigger input module 18.

The connection between the stimulation controller 14 and the stimulation feedback acquisition system 16 and the stimulation controller 14 and the reference trigger input module 18 is in the shown embodiment a direct and bidirectional connection.

However, also an indirect and/or unidirectional connection (i.e. with another component of the neuromodulation system 10 in between) would be generally possible.

The connection between stimulation controller 14 and the stimulation feedback acquisition system 16 and the stimulation controller 14 and the reference trigger input module 18 is established in the shown embodiment by a wireless network WSN.

However, also a cable bound connection would be generally possible.

Moreover, the stimulation feedback acquisition system 16 is connected to the reference trigger input module 18.

The connection between the stimulation feedback acquisition system 16 and the reference trigger input module 18 is in the shown embodiment a direct and bidirectional connection.

However, also an indirect and/or unidirectional connection (i.e. with another component of the neuromodulation 10 in between) would be generally possible.

The connection between the stimulation feedback acquisition system 16 and the reference trigger input module 18 is established in the shown embodiment by a wireless network WSN.

However, also a cable bound connection would be generally possible.

The stimulation controller 14 provides a stimulation signal to the stimulation element 12 (e.g., IPG).

The stimulation element 12 provides stimulation to the patient via a lead 20 comprising electrodes.

The lead 20 could comprise multiple electrodes.

A physiological response to the stimulation by the stimulation element 12 and the lead 20 comprising electrodes is recognized by the stimulation feedback acquisition system 16.

In particular, the response to the stimulation by the stimulation element 12 and the lead 20 is recognized by the sensor 16*b* of the stimulation feedback acquisition system 16.

The stimulation controller 14 provides a reference trigger signal.

The reference trigger signal is recorded by the feedback acquisition system 16.

In particular, the reference trigger signal is recognized by the sensor 16*b* of the stimulation feedback acquisition system 16.

In this embodiment, the reference trigger signal could be provided by the stimulation controller 14 at the same time as the stimulation signal to the stimulation element 12 is provided.

In alternative embodiments, the reference trigger signal could be provided by the stimulation controller 14 before the stimulation signal to the stimulation element 12 and the lead 20 is provided.

In alternative embodiments, the reference trigger signal could be provided by the stimulation controller 14 after the stimulation signal to the stimulation element 12 and the lead 20 is provided.

The time of recognizing the physiological response to the stimulation by the stimulation element 12 by the sensor 16*b* is recorded by the stimulation feedback acquisition base station 16*a*.

The reference trigger input module 18 characterizes the temporal relationship as part of the full recruitment curve between providing the reference trigger signal by the stimulation controller 14 and recognizing by the sensor 16*b* and the stimulation provided by the stimulation element 12 and the lead 20 and recognizing the response of stimulation by the sensor 16*b*.

In this embodiment, the temporal relationship characterized by the reference trigger input module 18 is a time delay.

In this embodiment, the reference trigger input module 18 enables correction of the time delay induced by the feedback acquisition system 16.

By utilizing the reference trigger input module 18, a reference trigger input on the basis of the time delay is provided for optimizing stimulation parameters for a certain type of movement.

In this embodiment, the characterization of the temporal relationship could enable synchronizing the clocks of the stimulation element 12 and/or the stimulation controller 14 and/or the feedback acquisition system 16, including the sensor 16*b* and/or the base station 16*a*, and/or the reference trigger input module 18 and/or the wireless network WSN.

Not shown in FIG. 1 is that the reference trigger signal could communicate the sensor 16*b* the relative time with respect to the stimulation by the stimulation element 12.

In general, it could be possible that the reference trigger signal is used to start data acquisition of the stimulation feedback acquisition system 16.

In general, it could be possible that the reference trigger signal is used to start data acquisition of the sensor 16*b* of the stimulation feedback acquisition system.

It could be generally possible that the reference trigger signal and the stimulation signal provided by the stimulation controller 14 are the same signal.

Not shown in FIG. 1 is that the neuromodulation system 10 could further comprise one or more subsystems, including but not limited to a programmer 22, a passive electrical component, a microprocessor, a wireless link WL, a communication module COM and/or a telemetry module TEL Not shown in FIG. 1 is that the communication module COM could be or could comprise a Bluetooth module BT and the telemetry module TEL could be or could comprise a Near Field Magnetic Induction (NFMI) module or a Near Field Electromagnetic Induction (NFEMI) module.

Not shown in FIG. 1 is that the reference trigger signal could be an electrical signal, a Bluetooth signal, a NFMI signal and/or a NFEMI signal.

Not shown in FIG. 1 is that the temporal relationship between all possible subsystems of the neuromodulation system 10 may be characterized by the reference trigger input module 18.

Not shown in FIG. 1 is that the clocks of said further subsystems of the neuromodulation system 10 may be synchronized.

Not shown in FIG. 1 is that in this embodiment, the sensor 16*b* is a surface EMG electrode.

In particular, in this embodiment the sensor 16*b* is a surface EMG electrode placed on the skin of the patient.

In particular, in this embodiment the sensor 16*b* is a surface EMG electrode placed on the skin of a leg of the patient P.

However, in general, the sensor 16*b* as a surface EMG electrode could be placed on the skin of any part of the body of a patient P.

In an alternative embodiment, an intramuscular EMG electrode could be used as a sensor 16*b*.

In an alternative embodiment, an electrode array (intramuscular or surface electrode array) could be used as the sensor 16*b*.

Not shown in FIG. 1 is that alternative sensors 16*b* of the feedback acquisition system 16 for measuring the physiological response to the stimulation could be or could comprise at least one of a sequence of event sensor and/or a motion sensor and/or an EMG, and/or a afferent signal sensor and/or an efferent signal sensor and/or impedance sensor and/or BCI and or camera-based system.

Not shown in FIG. 1 is that a sensor could be implemented as a camera-based system that detects muscular activation.

Not shown in FIG. 1 is that an implanted stimulation element and/or stimulation electrode and/or array of electrodes could also be used as a sensor.

Figure 2:
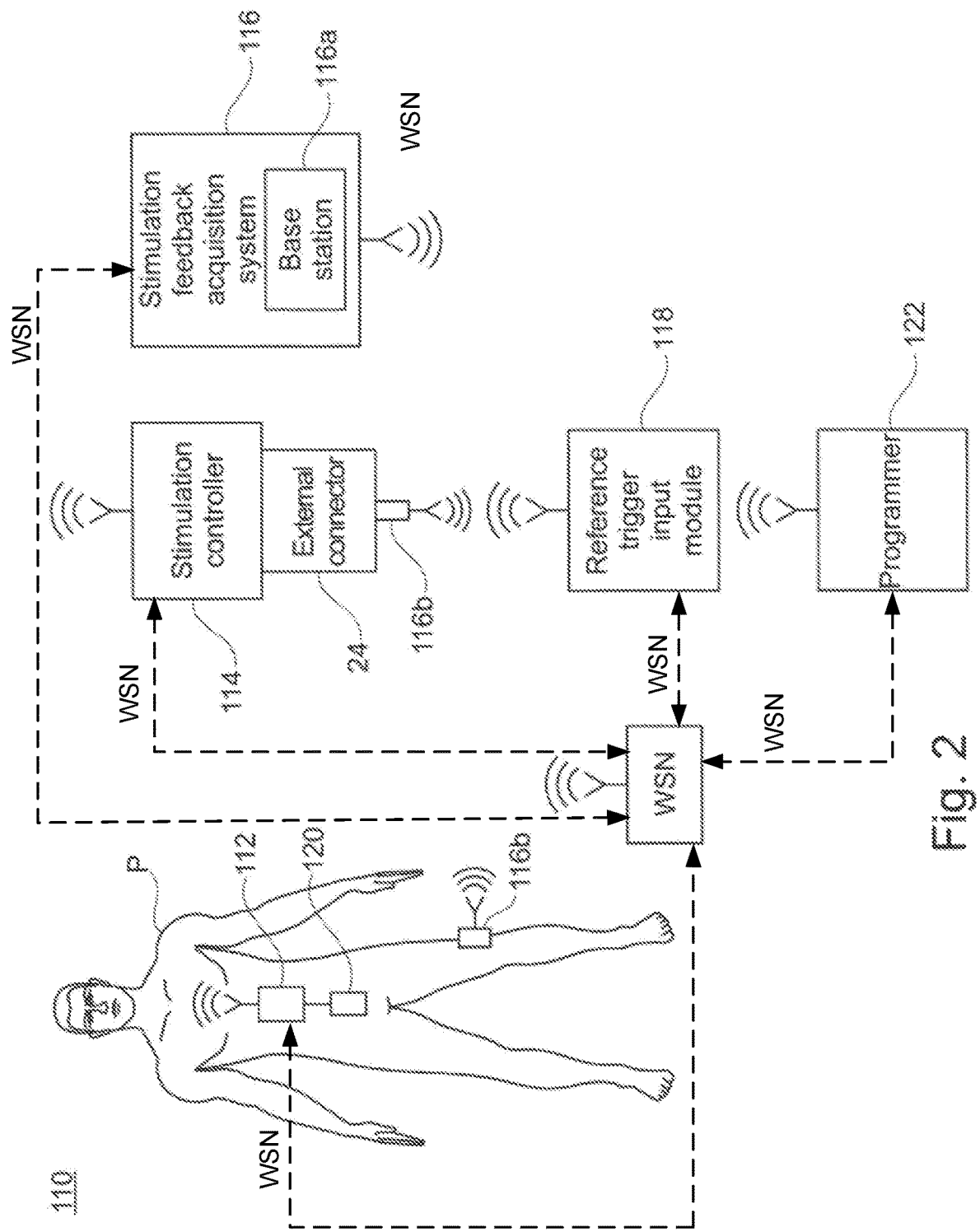
FIG. 2 a schematic illustration of a patient equipped with one embodiment of the neuromodulation system disclosed in FIG. 1 comprising two sensors and a connector.

FIG. 2 shows a schematic illustration of a patient P equipped the neuromodulation system 110 comprising two sensors 116*b* and a connector 24.

The neuromodulation system 110 comprises the structural and functional features as disclosed for neuromodulation system 10 in FIG. 1. The corresponding references are indicated as 100+x (e.g. stimulation element 112).

In this embodiment, the patient P is equipped with said neuromodulation system 110.

The neuromodulation system 110 additionally comprises a programmer 122.

In this embodiment, the programmer 122 is an application installed on a mobile device.

In general, other embodiments of a programmer 122 are possible.

The neuromodulation system 110 further comprises a connector 24.

In this embodiment, the connector 24 is an external connector 24.

Further, the neuromodulation system 110, in particular the stimulation feedback acquisition system 116, comprises two identical sensors 116*b*.

In this embodiment, the external connector 24 is connected to the stimulation feedback acquisition system 116.

In particular, one sensor 116*b* is mounted on the external connector 24.

One sensor 116*b* is placed on the skin of a patient P.

The two sensors 116*b* are synchronized.

In this embodiment, the programmer 122 is connected to the stimulation controller 114.

The connection between the programmer 122 and the stimulation controller 114 is in the shown embodiment a direct and bidirectional connection.

However, also an indirect and/or unidirectional connection (i.e. with another component of the neuromodulation 110 in between) would be generally possible.

The connection between the programmer 122 and the stimulation controller 114 is established in the shown embodiment by a wireless network WSN.

However, also a cable bound connection would be generally possible.

In this embodiment, the programmer 122 is also communicatively connected to the stimulation element 112 (e.g., IPG), the reference trigger input module 118 and/or the stimulation feedback acquisition system 116.

The connection between the programmer 122 and the stimulation element 112, the reference trigger input module 118 and the stimulation feedback acquisition system 116 is a direct and bidirectional connection.

The connection between the programmer 122 and the stimulation element 112, the reference trigger input module 118 and the stimulation feedback acquisition system 116 is established in the shown embodiment by a wireless network WSN.

However, also an indirect and/or unidirectional connection (i.e. with another component of the neuromodulation 110 in between) would be generally possible.

In general, the connection between the programmer 122 and the stimulation element 112, the reference trigger input module 118 and/or the stimulation feedback acquisition system 116 could be a wireless or cable-bound connection.

The stimulation controller 114 is connected to the external connector 24

In this embodiment, the stimulation controller 114 is directly connected to the external connector 24.

However, also an indirect connection between the external connector 24 and the stimulation controller 114 could be generally possible.

The programmer 122 programs the stimulation controller 114 to deliver a reference trigger signal.

The reference trigger signal provided by the stimulation controller 114 is recognized by the sensor 116b mounted on the external connector 24.

The time of recognizing the reference trigger signal by the sensor 116b mounted on the external connector 24 is recorded by the stimulation feedback acquisition base station 116a.

The programmer 122 programs the stimulation controller 114 to deliver stimulation.

The stimulation controller 114 provides a stimulation signal to the stimulation element 112.

The stimulation element 112 provides stimulation to the patient P via the lead 120 comprising electrodes.

A physiological response to the stimulation by the stimulation element 112 and the lead 120 comprising electrodes is recognized by the stimulation feedback acquisition system 116.

In particular, the response to the stimulation by the stimulation element 112 and the lead 120 is recognized by the sensor 116b placed on the skin of the patient P.

The time of recognizing the physiological response to the stimulation by the stimulation element 112 by the sensor 116b placed on the skin of the patient P is recorded to the stimulation feedback acquisition base station 116a.

The reference trigger input module 118 characterizes the temporal relationship as part of the full recruitment curve between providing the reference trigger signal by the stimulation controller 114 and recognizing by sensor 116b mounted on the external connector 24 and the stimulation provided by the stimulation element 112 and the lead 120 and recognizing the response of stimulation by the sensor 116b placed on the skin of the patient P.

In this embodiment, the characterization of the temporal relationship enables synchronizing the clocks of the stimulation element 112 and/or the stimulation controller 114 and/or the sensor 116b mounted on the external connector and/or the sensor 116b placed on the skin of the patient P and/or the stimulation feedback acquisition base station 116a, and/or the reference trigger input module 118.

In general, the programmer 122 could be used by a person, including but not limited to a therapist, physiotherapist, or patient to provide inputs to the stimulation controller 114, including but not limited to selecting, starting, and stopping a task or configuring stimulation parameters.

In particular, the programmer 122 could allow adjusting the stimulation parameters of a task, while the task is running.

Not shown in FIG. 2 is that the feedback acquisition system 16 could comprise two non-identical sensors 116b or more than 2 identical or non-identical sensors 116b.

Figure 3:
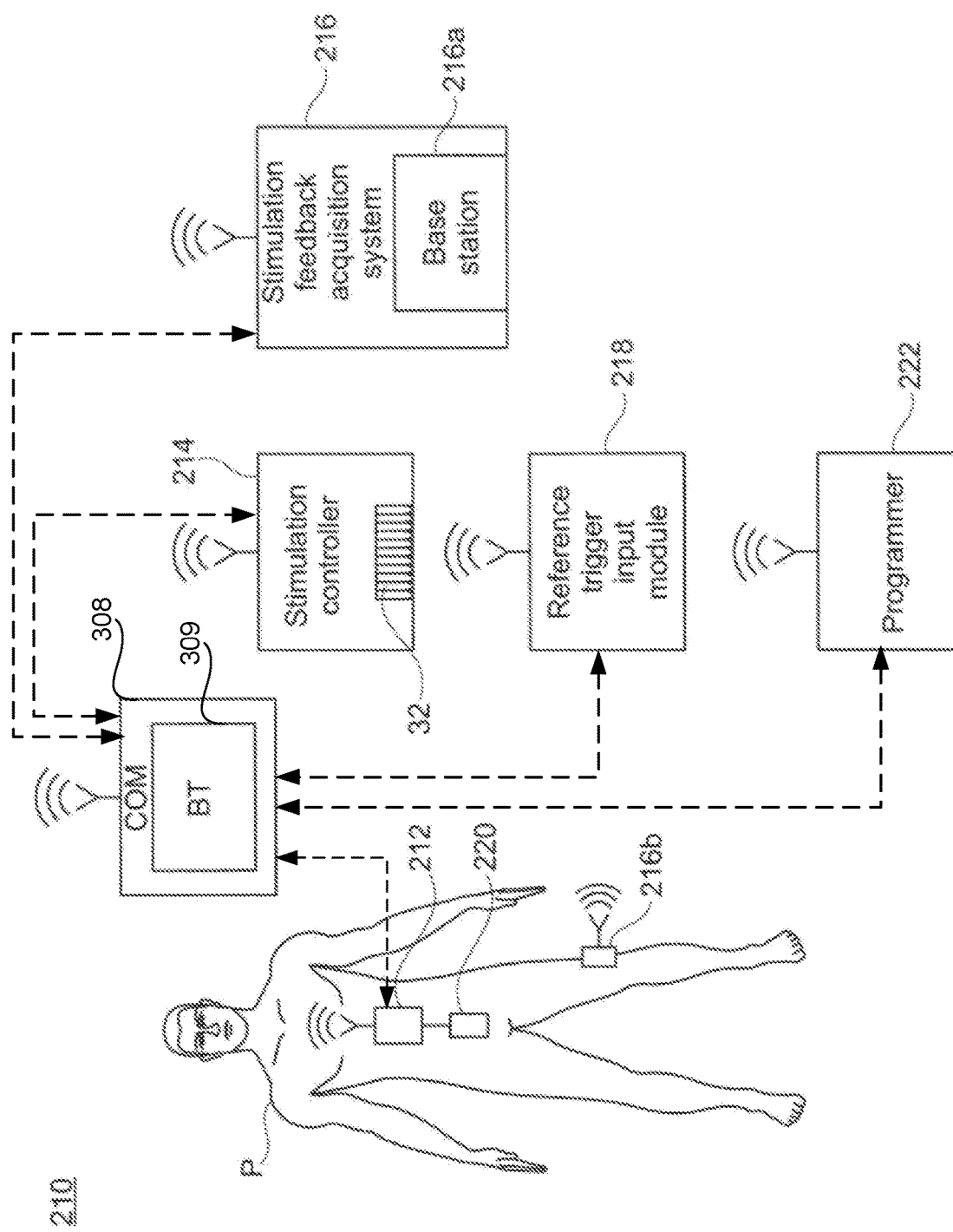
FIG. 3 a schematic illustration of a patient equipped with one embodiment the neuromodulation system disclosed in FIG. 1 comprising a communication module.

FIG. 3 shows a schematic illustration of a patient P equipped with the neuromodulation system 210 comprising a communication module COM.

The neuromodulation system 210 comprises the structural and functional features as disclosed for neuromodulation system 10 in FIG. 1. The corresponding references are indicated as 200+x (e.g. stimulation element 212).

In this embodiment, the patient P is equipped with a neuromodulation system 210.

The neuromodulation system 210 further comprises a communication module COM 208.

In this embodiment, the communication module COM 308 comprises a Bluetooth module BT 309.

The stimulation controller 214 comprises a Bluetooth interface 32.

The neuromodulation system 210 additionally comprises a programmer 222, with the structure and function of the programmer 122 as disclosed in FIG. 2.

The connection between the programmer 222 and the stimulation controller 214 is established in the shown embodiment by the communication module COM 308, i.e. the Bluetooth module BT.

In this embodiment also the stimulation element 212 (e.g., IPG), the stimulation controller 214, the stimulation feedback acquisition system 216 including the sensor 216b and/or the base station 216a and/or the reference trigger input module 218 are also connected via the Bluetooth module BT (shown by dashed lines).

However, also cable bound connections would be generally possible.

The programmer 222 programs the stimulation controller 214 to deliver a reference trigger signal via the Bluetooth interface 32.

The reference trigger signal is a Bluetooth signal.

The reference trigger signal, i.e. the Bluetooth signal, is communicated to the sensor 216b via the Bluetooth module BT 309.

The stimulation feedback acquisition base station 216a records the time of recording the Bluetooth signal by the sensor 216b.

The programmer 222 programs the stimulation controller 214 to deliver stimulation.

The stimulation controller 214 provides a stimulation signal to the stimulation element 212.

The stimulation element 212 provides stimulation to the patient P via the lead 220 comprising electrodes.

A physiological response to the stimulation by the stimulation element 212 and the lead 220 comprising electrodes is recognized by the stimulation feedback acquisition system 216.

In particular, the response to the stimulation by the stimulation element 212 and the lead 220 is recognized by the sensor 216b of the stimulation feedback acquisition system 216.

The stimulation feedback acquisition base station 216a records the time of recognizing the response to the stimulation by the sensor 216b.

Figure 4:
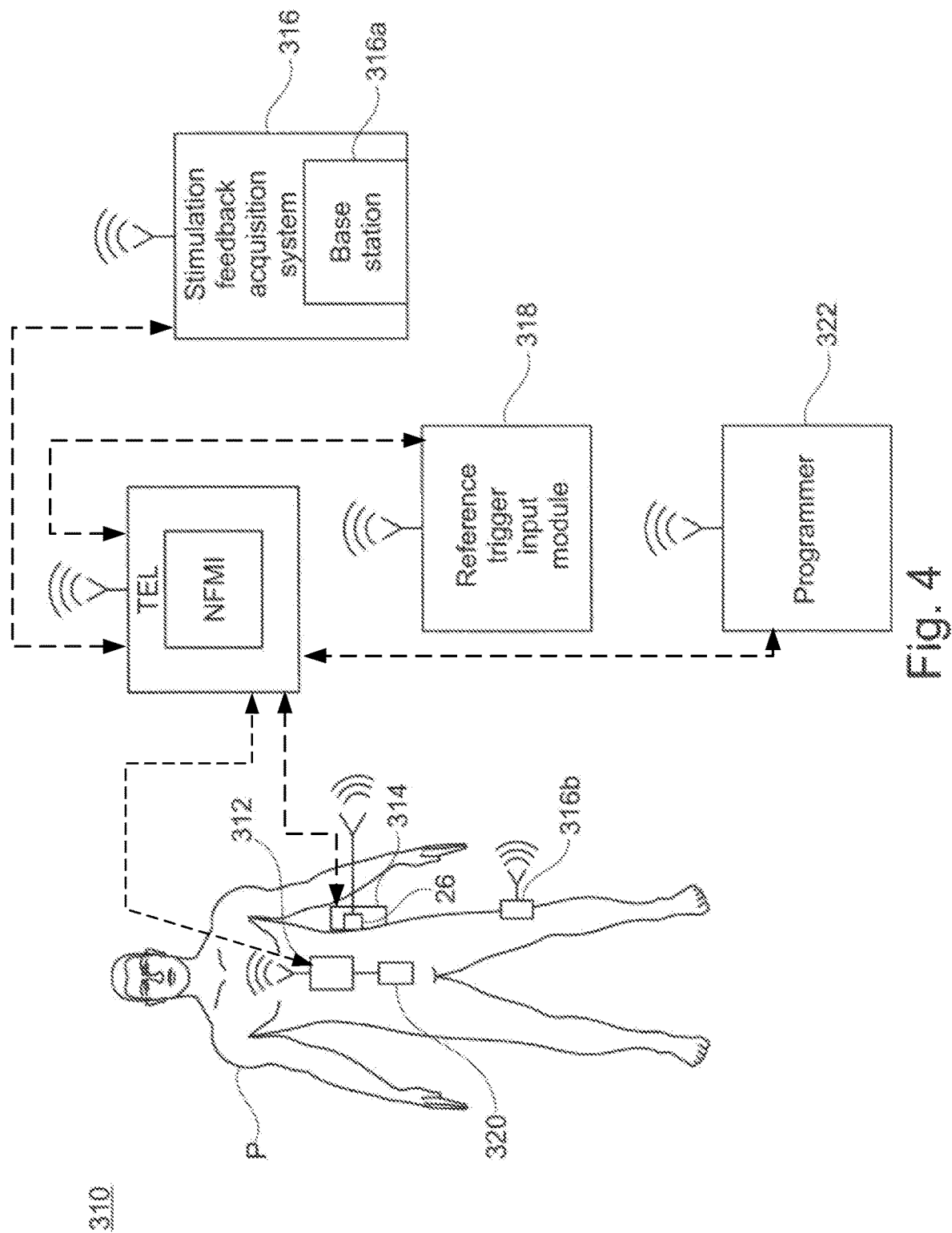
FIG. 4 a schematic illustration of a patient equipped with one embodiment of the neuromodulation system disclosed in FIG. 1 comprising a telemetry (NFMI) module.

FIG. 4 shows a schematic illustration of a patient P equipped with the neuromodulation system 310 comprising a telemetry module TEL.

The neuromodulation system 310 comprises the structural and functional features as disclosed for neuromodulation system 10 in FIG. 1. The corresponding references are indicated as 300+x (e.g. stimulation element 312).

In this embodiment, a patient P is equipped with a neuromodulation system 310.

In this embodiment, the neuromodulation system 310 comprises a telemetry module TEL.

The telemetry module TEL comprises a NFMI module.

The stimulation controller 314 comprises a NFMI interface 26.

The NFMI interface 26 is in contact with the skin of the patient P.

The neuromodulation system 310 additionally comprises a programmer 322, with the structure and function of the programmer 122 as disclosed in FIG. 2.

The connection between the programmer 322 and the stimulation controller 314 is established in the shown embodiment via the NFMI module (dashed line).

In this embodiment also the stimulation element 312, the stimulation controller 314, the feedback acquisition system 316 including the sensor 316b and/or the base station 316a, and/or the reference trigger input module 318 are also connected via the NFMI module (shown by dashed lines).

However, also cable bound connections and/or other wireless connections would be generally possible.

The programmer 322 programs the stimulation controller 314 to deliver a reference trigger signal.

The stimulation controller 314 provides a reference trigger signal via the NFMI interface 26.

The reference trigger signal is a NFMI signal.

The NFMI signal is recorded by the sensor 316b.

It is generally possible, that the NFMI signal is partially or fully transmitted via the body of the patient P, including the skin, and recorded by the sensor 316b.

The stimulation feedback acquisition base station 316a records the time of recording the NFMI signal by the sensor 316b.

The programmer 322 programs the stimulation controller 314 to deliver stimulation.

The stimulation controller 314 provides a stimulation signal to the stimulation element 312.

The stimulation element 312 provides stimulation to the patient P via the lead 320 comprising electrodes.

A physiological response to the stimulation by the stimulation element 312 and the lead 320 comprising electrodes is recognized by the feedback acquisition system 316.

In particular, the response to the stimulation by the IPG 312 and the lead 320 is recognized by the sensor 316b of the feedback acquisition system 316.

The stimulation feedback acquisition base station 316a records the time of recognizing the response to the stimulation by the sensor 316b.

The time of recognizing the physiological response to the stimulation by the IPG 312 by the sensor 316b is recorded by the stimulation feedback acquisition base station 316a.

The characterization of the temporal relationship enables synchronizing the clock of the programmer 322 and the IPG 312 and/or the stimulation controller 314 and/or the feedback acquisition system 316 and/or the reference trigger input module 318.

Not shown in FIG. 4 is that the telemetry module TEL may alternatively and/or additionally comprise one or more of a Medical Implant Communication System (MICS).

MICS is a low-power, short-range, high-data-rate, 401-406 MHz (the core band is 402-405 MHz) communication network.

Not shown in FIG. 4 is that the telemetry module TEL may alternatively and/or additionally comprise one or more of a Medical Data Service System (MEDS).

MEDS systems may operate in spectrum within the frequency bands 401 MHz to 402 MHz and 405 MHz to 406 MHz.

It is not shown in FIG. 4 that any other type of telemetry module known in the art is generally possible.

Figure 5:
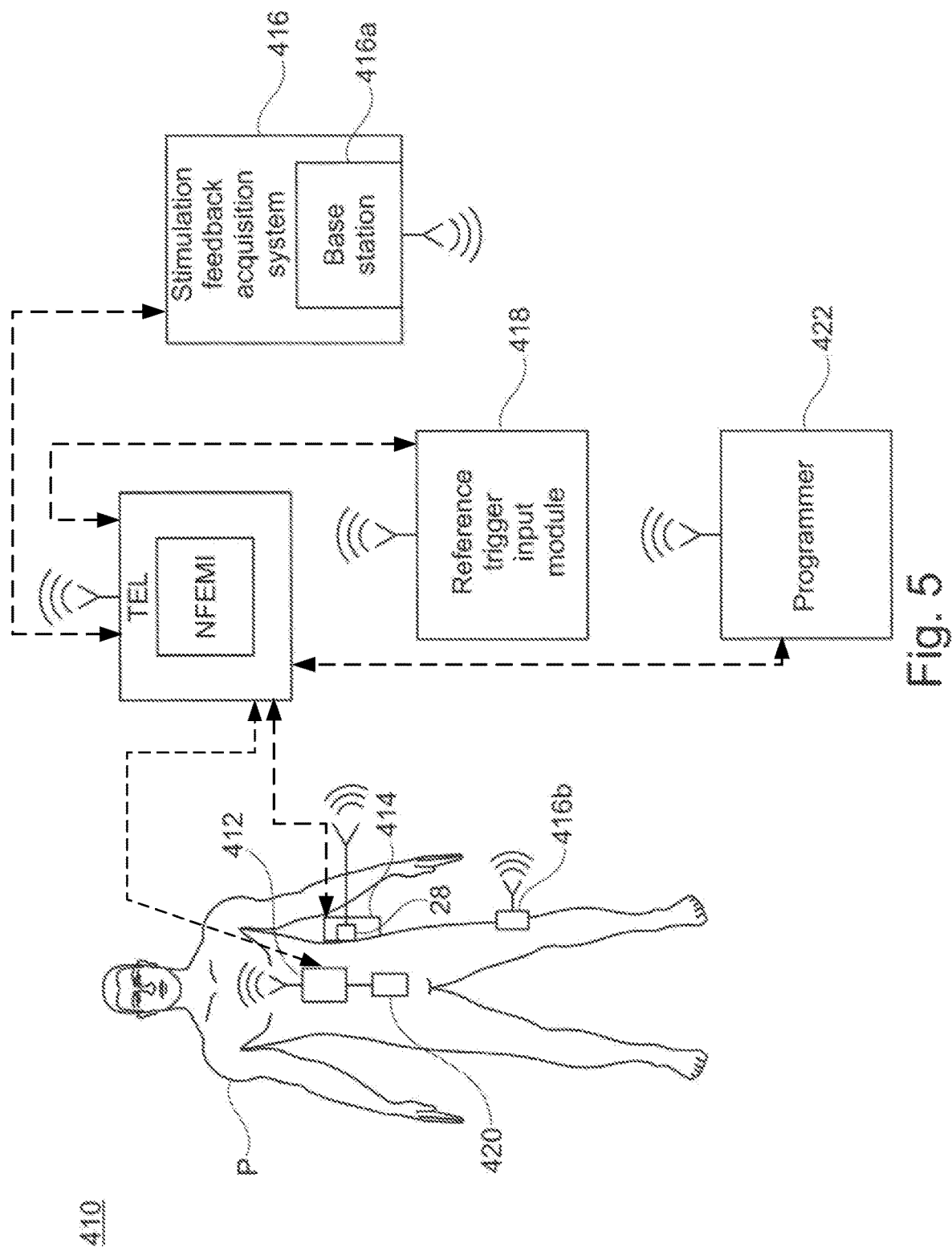
FIG. 5 a schematic illustration of a patient equipped with a further embodiment of the neuromodulation system disclosed in FIG. 1 comprising a telemetry (NFEMI) module.

FIG. 5 shows a perspective view of a patient P equipped with the neuromodulation system 410 comprising a telemetry module TEL The neuromodulation system 410 comprises the structural and functional features as disclosed for neuromodulation system 10 in FIG. 1. The corresponding references are indicated as 400+x (e.g. stimulation element 412).

In this embodiment, a patient P is equipped with a neuromodulation system 410.

In this embodiment, the neuromodulation system 410 comprises a telemetry module TEL.

The telemetry module TEL comprises an NFEMI module.

The stimulation controller 414 comprises an NFEMI interface 28.

The NFEMI interface 28 is in contact with the skin of the patient P.

The neuromodulation system 410 additionally comprises a programmer 422, with the structure and function of the programmer 122 as disclosed in FIG. 2.

The connection between the programmer 422 and the stimulation controller 414 is established in the shown embodiment via the NFEMI module (dashed line).

In this embodiment also the stimulation element 412, the stimulation controller 414 and/or the NFEMI interface 28, the feedback acquisition system 416 including the sensor 416b and the base station 416a and the reference trigger input module 418 are connected via the NFEMI module (shown by dashed lines).

However, also cable bound connections and/or other wireless connections would be generally possible.

The programmer 422 programs the stimulation controller 414 to provide a reference trigger signal.

The reference trigger signal is an NFEMI signal.

The NFEMI signal is provided by the NFEMI interface 28.

The NFEMI signal is transmitted via the skin/body of the patient P.

The NFEMI signal could alternatively and/or additionally be transmitted via air.

The NFEMI signal is recorded by the sensor 416b.

The stimulation feedback acquisition base station 416a records the time of recording the NFEMI signal by the sensor 416b.

The programmer 422 programs the stimulation controller 414 to deliver stimulation.

The stimulation controller 414 provides a stimulation signal to the IPG 412.

The stimulation element 412 provides stimulation to the patient P via the lead 420 comprising electrodes.

A physiological response to the stimulation by the stimulation element 412 and the lead 420 comprising electrodes is recognized by the stimulation feedback acquisition system 416.

In particular, the response to the stimulation by the stimulation element 412 and the lead 420 is recognized by the sensor 416b of the stimulation feedback acquisition system 416.

The stimulation feedback acquisition base station 416a records the time of recognizing the response to the stimulation by the sensor 416b.

The reference trigger input module 418 characterizes the temporal relationship as part of the full recruitment curve between providing the reference trigger signal, i.e. the NFEMI signal by the NFEMI interface 28 of the stimulation controller 414 and recognizing by the sensor 416b and the stimulation provided by the IPG 412 and the lead 420 and recognizing the response of stimulation by the sensor 416b.

In this embodiment, the characterization of the temporal relationship enables synchronizing the clocks of the stimulation element 412 and/or the stimulation controller 414 and/or the NFEMI interface 28 and/or the sensor 416b and/or the base station 416a of the stimulation feedback acquisition system 416, and/or the reference trigger input module 418 and/or the programmer 422.

Figure 6:
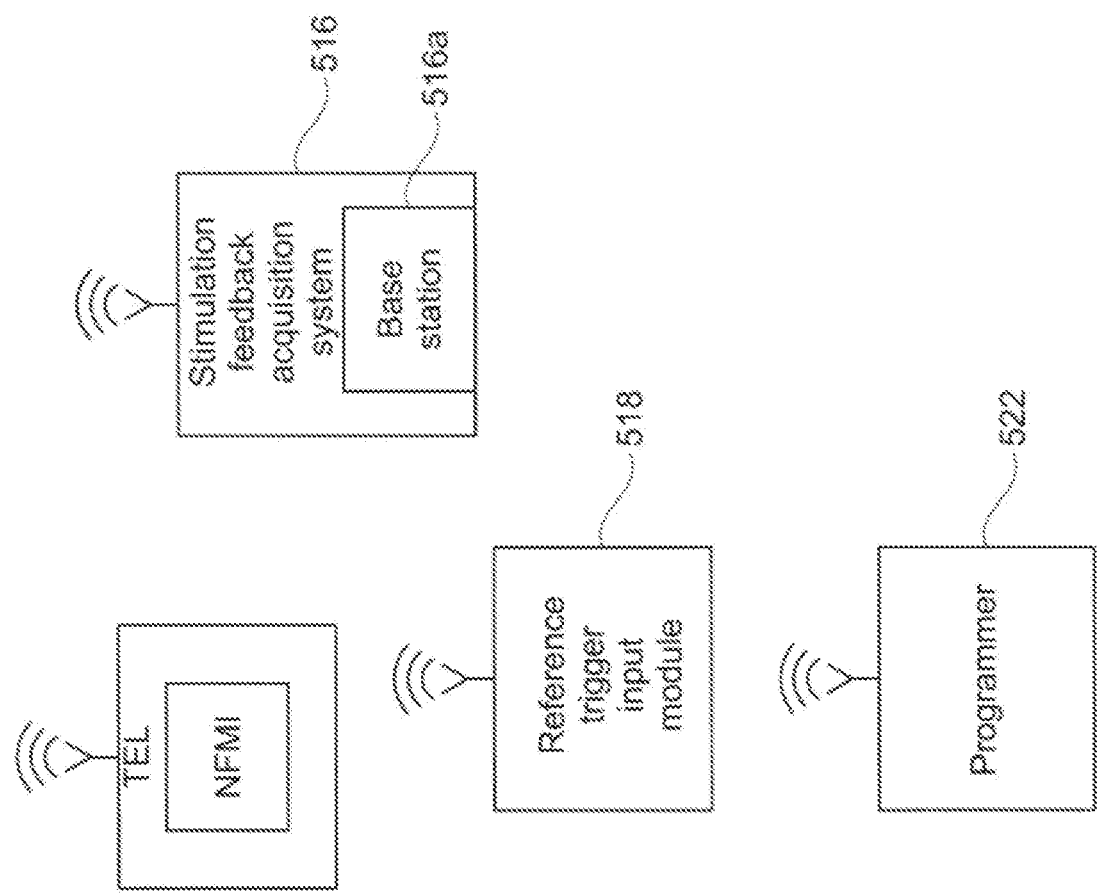
FIG. 6 shows a schematic illustration of a patient equipped with one embodiment of the neuromodulation system disclosed in FIG. 1 comprising a passive electrical component.
Figure 6:
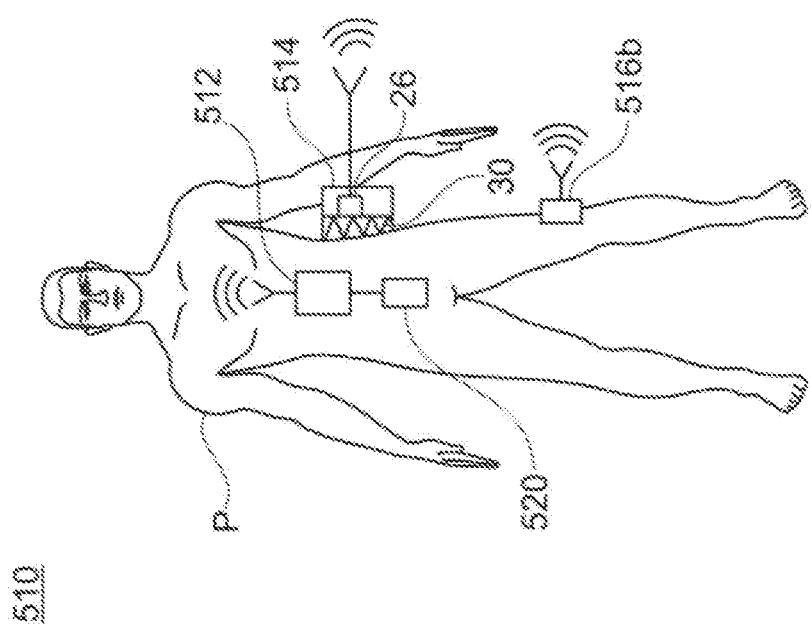

FIG. 6 shows a perspective view of a patient P equipped with the neuromodulation system 510 comprising a passive electrical component 30.

The neuromodulation system 510 comprises the structural and functional features as disclosed for neuromodulation systems 10 and/or 310 in FIGS. 1 and 4. The corresponding references are indicated as 500+x or 200+x (e.g. stimulation element 512).

In this embodiment, a patient P is equipped with a neuromodulation system 510.

In this embodiment, the neuromodulation system 510 comprises a passive electrical component 30.

In this embodiment, the passive electrical component 30 is included in a sticker.

In this embodiment, the sticker is in placed on the skin of the patient P.

In general, other embodiments of passive electrical component 30 are possible.

The sticker is in contact to the stimulation controller 514.

In this embodiment, the sticker is in direct contact to the stimulation controller 514.

In this embodiment, the sticker is placed between the skin of the patient P and the stimulation controller 514.

The programmer 522 programs the stimulation controller 514 to deliver a reference trigger signal.

The reference trigger signal is a NFMI signal.

The NFMI signal is delivered by the NFMI interface 26 of the stimulation controller 514.

The NFMI signal is converted into an electrical signal by the sticker 30.

The electrical signal is transmitted via the body of the patient P.

The electrical signal is recorded by the sensor 516b.

The stimulation feedback acquisition base station 516a records the time of recording the NFMI signal by the sensor 516b.

In other words, the passive electrical component 30, i.e. the sticker, converts the NFMI signal into an electrical signal and the signal is recorded by the stimulation feedback acquisition system 516.

The programmer 522 programs the stimulation controller 514 to deliver stimulation.

The stimulation controller 514 provides a stimulation signal to the stimulation element 512.

The stimulation element 512 provides stimulation to the patient P via the lead 520 comprising electrodes.

A physiological response to the stimulation by the stimulation element 512 and the lead 520 comprising electrodes is recognized by the feedback acquisition system 516.

In particular, the response to the stimulation by the IPG 512 and the lead 520 is recognized by the sensor 516b of the stimulation feedback acquisition system 516.

The stimulation feedback acquisition base station 516a records the time of recognizing the response to the stimulation by the sensor 516b.

It is not shown in FIG. 6 that the signal provided by the telemetry module TEL could be another signal than a NFMI signal, and the signal converted by the sticker could be another signal than an electrical signal.

It is not shown in FIG. 6 that the passive electrical component may alternatively and/or additionally be configured and arranged to be inserted and/or integrated into and/or onto the clothing of the patient, including but not limited to a top, a longsleeve, a pullover, a jacket, one or more gloves, armlets, socks, tights, a belt and/or a pouch worn by the patient equipped with the system.

Figure 7:
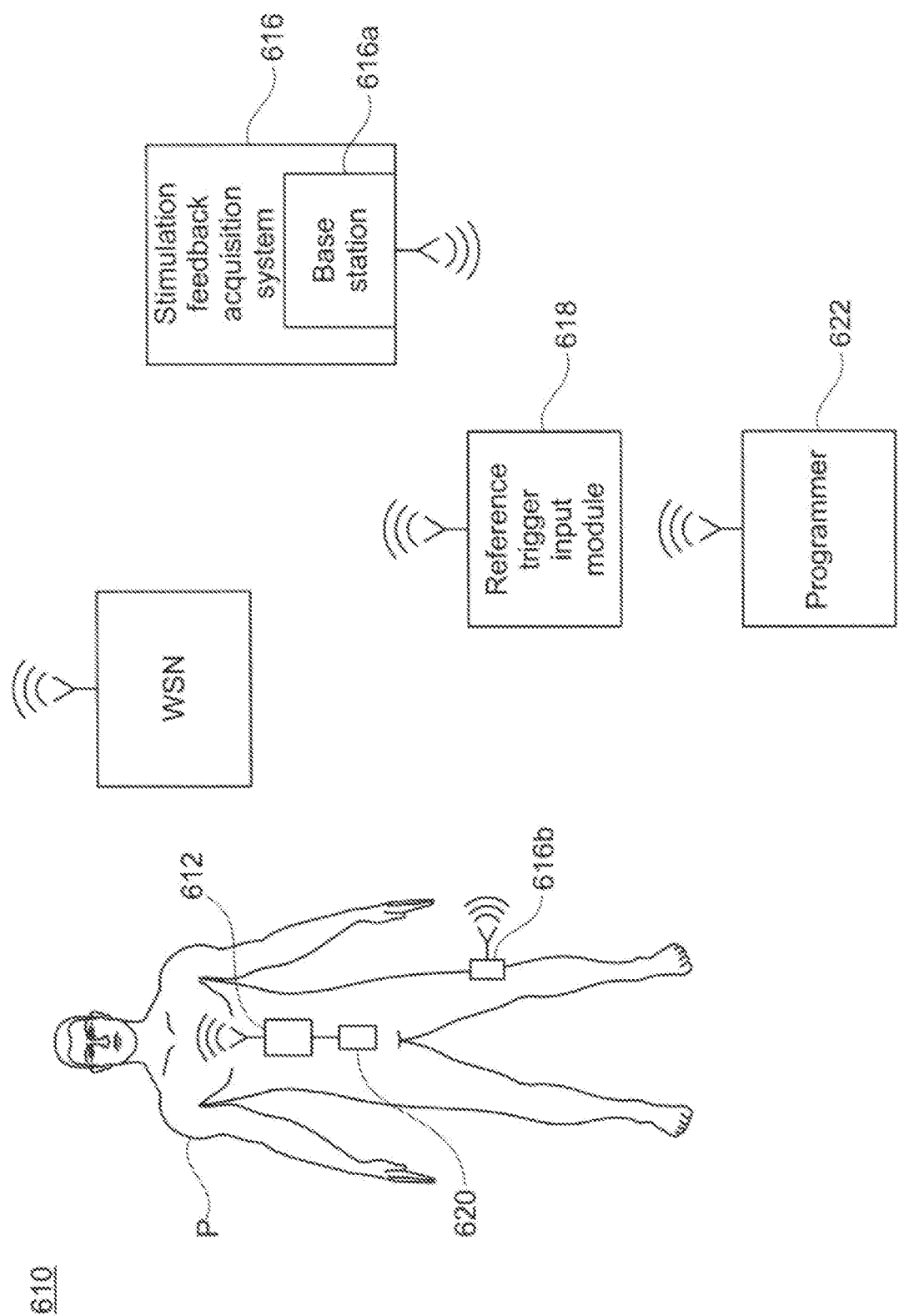
FIG. 7 shows a schematic illustration of a patient equipped with one embodiment of a neuromodulation system disclosed in FIG. 1 using an electrical reference trigger signal provided by the IPG.

FIG. 7 shows a perspective view of a patient P equipped with the neuromodulation system 610 using an electrical reference trigger signal provided by the IPG 612.

The neuromodulation system 610 comprises the structural and functional features as disclosed for neuromodulation system 10 in FIG. 1. The corresponding references are indicated as 600+x (e.g. stimulation element 612).

In this embodiment, a patient P is equipped with a neuromodulation system 610.

The neuromodulation system 610 further comprises a programmer 622, with the structure and function of the programmer 122 as disclosed in FIG. 2.

The stimulation element 612 (e.g., IPG) is implanted close to the skin of the patient P.

In particular, the IPG 612 is implanted less than 2 cm under the skin of the patient P.

In an alternative embodiment, the IPG 612 could be implanted deeper in the body of the patient P.

The programmer 622 programs the stimulation controller (not shown) to deliver a reference trigger signal.

In this embodiment, the reference trigger signal is an electrical trigger signal.

In this embodiment, the reference trigger signal is delivered via a casing of the stimulation element 612.

In particular, for the reference trigger signal a waveform is chosen, which does not lead to stimulation of the patient P near the stimulation element 612.

The reference trigger signal, i.e. the electrical trigger signal, pulls down or pushes up the skin potential of the patient P.

A change in skin potential is recorded by the sensor 616b of the stimulation feedback acquisition system 616.

In other words, an under-threshold signal is provided by the casing of the stimulation element 612.

The under-threshold signal does not lead to stimulation of the patient P but is detectable by the stimulation feedback acquisition system 616 as a reference trigger signal.

The time of recognizing the change in skin potential in response to the reference trigger signal provided by the casing of the stimulation element 612 by the sensor 616b is recorded by the stimulation feedback acquisition base station 616a.

The programmer 622 programs the stimulation controller (not shown) to deliver stimulation.

The stimulation controller 614 provides a stimulation signal to the stimulation element 612.

The stimulation element 612 provides stimulation to the patient P via the lead 620 comprising electrodes.

A physiological response to the stimulation by the stimulation element 612 and the lead 620 comprising electrodes is recognized by the stimulation feedback acquisition system 616.

In particular, the physiological response to the stimulation by the stimulation element 612 and the lead 620 is recognized by the sensor 616b of the stimulation feedback acquisition system 616.

The time of recognizing the physiological response to the stimulation by the stimulation element 612 and the lead 620 by the sensor 616b is recorded by the stimulation feedback acquisition base station 616a.

The reference trigger input module 618 characterizes the temporal relationship as part of the full recruitment curve between providing the reference trigger signal by the casing of the stimulation element 612 and recognizing the evoked skin potentials by the sensor 616b and the stimulation provided by the stimulation element 612 and the lead 620 and recognizing the response to the stimulation by the sensor 616b.

Not shown in FIG. 7 is that the reference trigger signal could alternatively and/or additionally be provided by the lead 620 comprising electrodes.

Note that the example control and estimation routines included herein can be used with various system configurations. The control methods and routines disclosed herein may be stored as executable instructions in non-transitory memory and may be carried out by a neuromodulation system 10, 110, 210, 310, 410, 510, 610 e.g. as a part of the stimulation system 12, 112, 212, 312, 412, 512, 612, the stimulation controller 14, 114, 214, 314, 414, 514, 614, the stimulation feedback acquisition system 16, 116, 216, 316, 416, 516, 616, the reference input module 18, 118, 218, 318, 418, 518, 618, the programmer 22, 122, 222, 322, 422, 522, 622 and other system hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of a computer readable storage medium in the stimulation controller 14, 114, 214, 314, 414, 514, 614, where the described actions are carried out by executing the instructions in a neuromodulation system 10, 110, 210, 310, 410, 510, 610 including the various hardware components.

REFERENCES

10 Neuromodulation system
12 Stimulation element/IPG
14 Stimulation controller
16 Stimulation feedback acquisition system
16a (Stimulation feedback aquisition) base station
16b Sensor/surface EMG electrode
18 Reference trigger input module
20 Lead
22 Programmer
24 Connector/external connector
26 NFMI interface
28 NFEMI interface
30 Passive electrical component/sticker
32 Bluetooth interface
110 Neuromodulation system
112 Stimulation element/IPG
114 Stimulation controller
116 Stimulation feedback acquisition system
116a (Stimulation feedback acquisition) base station
116b Sensor/surface EMG electrode
118 Reference trigger input module
120 Lead
122 Programmer
210 Neuromodulation system
212 Stimulation element/IPG
214 Stimulation controller
216 Stimulation feedback acquisition system
216a (Stimulation feedback acquisition) base station
216b Sensor/surface EMG electrode
218 Reference trigger input module
220 Lead
222 Programmer
308 Communication module COM
309 Bluetooth module BT
310 Neuromodulation system
312 Stimulation element/IPG
314 Stimulation controller
316 Stimulation feedback acquisition system
316a (Stimulation feedback acquisition) base station
316b Sensor/surface EMG electrode
318 Reference trigger input module
320 Lead
322 Programmer
410 Neuromodulation system
412 Stimulation element/IPG
414 Stimulation controller
416 Stimulation feedback acquisition system
416a (Stimulation feedback acquisition) base station
416b Sensor/surface EMG electrode
418 Reference trigger input module
420 Lead
422 Programmer
510 Neuromodulation system
512 Stimulation element/IPG
514 Stimulation controller
516 Stimulation feedback acquisition system
516a (Stimulation feedback acquisition) base station
516b Sensor/surface EMG electrode
518 Reference trigger input module
520 Lead
522 Programmer
610 Neuromodulation system
612 Stimulation element/IPG
614 Stimulation controller
616 Stimulation feedback acquisition system
616a (Stimulation feedback acquisition) base station
616b Sensor/surface EMG electrode
618 Reference trigger input module
620 Lead 622 Programmer
P Patient
BT Bluetooth
CNS Central Nervous System
COM Communication module
EES Epidural Electrical Stimulation
FES Functional Electrical Stimulation
MICS Medical Implant Communication System
MEDS Medical Data Service System
NFMI Near Field Magnetic Induction
NFEMI Near-field electromagnetic induction
PNS Peripheral Nervous System
WL Wireless link
WSN Wireless network
TEL Telemetry module

The invention claimed is:

1. A neuromodulation system comprising:
   at least one stimulation element;
   at least one stimulation controller; and
   at least one stimulation feedback acquisition system;
   wherein the at least one stimulation controller is configured to generate a reference trigger signal and stimulation control signals to the stimulation element;
   wherein the at least one stimulation feedback acquisition system includes a reference trigger input module configured to characterize a time delay between a provided stimulation, via the stimulation element, and the reference trigger signal provided by the stimulation controller.

2. The neuromodulation system of claim 1, wherein the characterization of the temporal relationship enables synchronizing the clocks of one or more of the stimulation element, the stimulation controller, the stimulation feedback acquisition system and the reference trigger input module.

3. The neuromodulation system of claim 1, wherein the at least one stimulation feedback acquisition system comprises a stimulation feedback acquisition base station and at least one sensor; and wherein the sensor is any of a sequence of event sensor, a motion sensor, a EMG, an afferent signal sensor, an efferent signal sensor, an impedance sensor, an EEG, a BCI, and a camera-based sensor.

4. The neuromodulation system according to claim 1, wherein the stimulation feedback acquisition system comprises two identical or non-identical sensors; and wherein the two sensors are synchronized.

5. The neuromodulation system of claim 1, wherein the neuromodulation system comprises one or more subsystems, wherein the subsystems comprise at least one of a programmer, a passive electrical means, a microprocessor, a wireless link (WL), a communication module (COM) and a telemetry module (TEL) module.

6. The neuromodulation system of claim 5, wherein the communication module (COM) comprises a Bluetooth module (BT) and the telemetry module (TEL) comprises any of a Near Field Magnetic Induction (NFMI) module or a Near Field Electromagnetic Induction (NFEMI) module.

7. The neuromodulation system of claim 1, wherein the stimulation controller is configured and arranged to provide a reference trigger signal; and wherein the reference trigger signal is recorded by the stimulation feedback acquisition system.

8. The neuromodulation system of claim 7, wherein the reference trigger signal is any of an electrical signal, a Bluetooth signal, a NFMI signal and a NFEMI signal.

9. The neuromodulation system of claim 7, wherein the reference trigger signal is a NFMI signal, and wherein the stimulation controller includes a passive electrical component configured and arranged to convert a NFMI signal into an electrical signal, wherein the electrical signal is recorded by the stimulation feedback acquisition system.

10. The neuromodulation system of claim 9, wherein the passive electrical component is a sticker; and wherein the sticker is placed on the skin of a patient.

11. The neuromodulation system of claim 9, wherein the passive electrical component is configured to be integrated into a clothing of the patient.

12. The neuromodulation system of claim 1, wherein the stimulation element is configured and arranged to provide an under-threshold signal, wherein the under-threshold signal does not lead to stimulation of a subject but is detectable by the stimulation feedback acquisition system as a reference trigger signal.

13. The neuromodulation system of claim 1, wherein the stimulation controller is configured and arranged to be connected to a connector; wherein the connector is connected to the stimulation feedback acquisition system.

14. The neuromodulation system of claim 12, wherein the connector is an external connector; and wherein a sensor is mounted on the external connector, the sensor configured to recognize a reference trigger signal provided by the stimulation controller.

15. The neuromodulation system of claim 14, wherein the stimulation feedback acquisition base station records a time of recognizing the reference trigger signal by the sensor.

16. The neuromodulation system of claim 1, further comprising a programmer communicatively coupled to one or more of the stimulation controller, the stimulation element, the reference trigger input module, and the stimulation feedback acquisition system.

17. The neuromodulation system of claim 16, wherein the programmer is an application installed on a mobile device.

18. The neuromodulation system of claim 16, wherein the programmer is configured to program the stimulation controller to deliver one or more of the provided stimulation and a reference trigger signal.

* * * * *